(12) United States Patent
Behan et al.

(10) Patent No.: US 8,603,188 B2
(45) Date of Patent: *Dec. 10, 2013

(54) MEDICAL DEVICE SUITABLE FOR TREATING REFLUX FROM A STOMACH TO AN OESOPHAGUS

(75) Inventors: Niall Behan, Kilcolgan (IE); Donal Devery, Oranmore (IE); Sean Finnegan, Newry (GB); Edwin Lyons, Newcastle (IE); Enda McLaughlin, Kinvara (IE)

(73) Assignee: Vysera Biomedical Limited, Galway (IE)

( * ) Notice: Subject to any disclaimer, the term of this patent is extended or adjusted under 35 U.S.C. 154(b) by 35 days.

This patent is subject to a terminal disclaimer.

(21) Appl. No.: 12/837,023

(22) Filed: Jul. 15, 2010

(65) Prior Publication Data

US 2010/0298951 A1  Nov. 25, 2010

Related U.S. Application Data

(63) Continuation of application No. 11/643,698, filed on Dec. 22, 2006.

(60) Provisional application No. 60/752,881, filed on Dec. 23, 2005.

(51) Int. Cl.
*A61F 2/04* (2013.01)
(52) U.S. Cl.
USPC .................................................. 623/23.68
(58) Field of Classification Search
USPC ............ 623/23.64, 23.65, 23.67, 23.68, 23.7
See application file for complete search history.

(56) References Cited

U.S. PATENT DOCUMENTS

| | | | |
|---|---|---|---|
| 4,271,827 A | 6/1981 | Angelchik | 600/37 |
| 4,747,849 A | 5/1988 | Galtier | 623/23 |
| 4,846,836 A | 7/1989 | Reich | 623/23 |
| 5,314,473 A | 5/1994 | Godin | 623/23 |
| 5,549,657 A | 8/1996 | Stern et al. | 604/537 |
| 5,653,747 A | 8/1997 | Dereume | 623/1 |
| 5,887,594 A | 3/1999 | LoCicero, III | 128/898 |
| 6,096,070 A | 8/2000 | Ragheb et al. | 623/1 |

(Continued)

FOREIGN PATENT DOCUMENTS

| | | |
|---|---|---|
| WO | WO00/12027 | 3/2000 |
| WO | WO02/094132 | 11/2002 |

(Continued)

*Primary Examiner* — Manuel Mendez
*Assistant Examiner* — Nathan R Price
(74) *Attorney, Agent, or Firm* — Choate, Hall & Stewart LLP; Andrea L. C. Robidoux; Daniel S. Matthews

(57) ABSTRACT

A medical treatment device (200), for treating reflux from a stomach (201) to an esophagus (202) and for delivering a therapeutic agent to an inner surface of the esophagus (202), comprises a valve member (203), a lining member (204), and a support member (205). The valve member (203) is movable between a closed configuration and an open configuration, in which the valve member (203) facilitates passage of material between the esophagus (202) and the stomach (201). The valve member (203) is biased towards the closed configuration and gradually moves over a period of 4 to 10 secs from the open configuration to the closed configuration. The support member (205) supports the device (200) relative to the esophagus (202) and the stomach (201). The lining member (204) lines part of the inner surface of the esophagus (202) for delivery of a therapeutic agent to the esophagus (202).

25 Claims, 33 Drawing Sheets

(56) References Cited

U.S. PATENT DOCUMENTS

| | | | |
|---|---|---|---|
| 6,254,642 B1 | 7/2001 | Taylor | 623/23 |
| 6,264,700 B1 | 7/2001 | Kilcoyne et al. | 623/23 |
| 6,302,917 B1 | 10/2001 | Dua et al. | 623/23 |
| 6,432,040 B1 | 8/2002 | Meah | 600/37 |
| 6,544,291 B2 | 4/2003 | Taylor | 623/23 |
| 6,558,429 B2 | 5/2003 | Taylor | 623/23 |
| 6,669,713 B2 | 12/2003 | Adams | 606/213 |
| 6,726,696 B1 | 4/2004 | Houser et al. | 606/151 |
| 6,746,489 B2 | 6/2004 | Dua et al. | 623/23 |
| 6,790,237 B2 | 9/2004 | Stinson | 623/23 |
| 6,908,447 B2 | 6/2005 | McAweeney et al. | 604/9 |
| 6,921,361 B2 | 7/2005 | Suzuki et al. | 600/106 |
| 6,921,378 B2 | 7/2005 | O'Keefe et al. | 604/9 |
| 6,958,079 B1 | 10/2005 | Taylor et al. | 623/23 |
| 6,960,233 B1 | 11/2005 | Berg et al. | 623/23 |
| 7,087,088 B2 | 8/2006 | Berg et al. | 623/23 |
| 2001/0020189 A1 | 9/2001 | Taylor | 623/23 |
| 2001/0020190 A1 | 9/2001 | Taylor | 623/23 |
| 2003/0060894 A1 | 3/2003 | Kua et al. | 623/23 |
| 2003/0188755 A1 | 10/2003 | Milbocker | 128/898 |
| 2003/0199730 A1 | 10/2003 | Silverman et al. | 600/29 |
| 2004/0044357 A1 | 3/2004 | Gannoe et al. | 606/194 |
| 2004/0199262 A1 | 10/2004 | Dua et al. | 623/23 |
| 2004/0225247 A1 | 11/2004 | Pugsley et al. | 602/41 |
| 2004/0225373 A1 | 11/2004 | Pugsley et al. | 623/23 |
| 2005/0075727 A1* | 4/2005 | Wheatley | 623/2.17 |
| 2005/0228505 A1 | 10/2005 | Cornet et al. | 623/23 |
| 2006/0041189 A1 | 2/2006 | Vancaillie | 600/154 |
| 2006/0041319 A1 | 2/2006 | Taylor et al. | 623/23 |
| 2006/0135971 A1 | 6/2006 | Swanstrom et al. | 606/153 |
| 2006/0142789 A1 | 6/2006 | Lehman et al. | 606/153 |

FOREIGN PATENT DOCUMENTS

| | | |
|---|---|---|
| WO | WO03/011179 | 2/2003 |
| WO | WO03/030782 | 4/2003 |
| WO | WO2005/060869 | 7/2005 |

\* cited by examiner

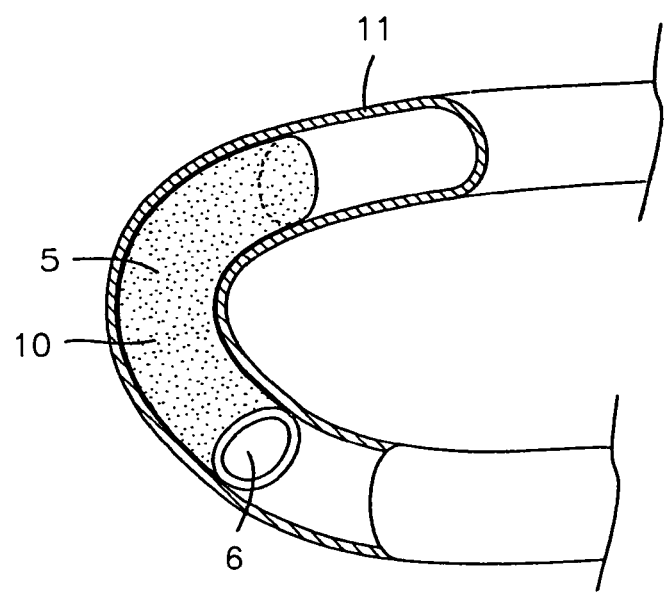

FIG. 10(a)
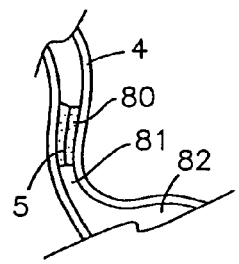
FIG. 10(b)  FIG. 10(c)  FIG. 10(d)
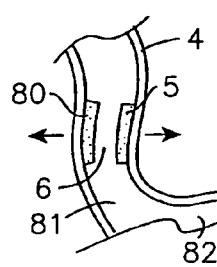 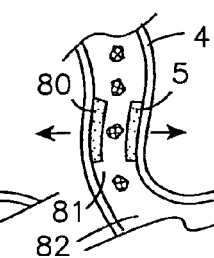 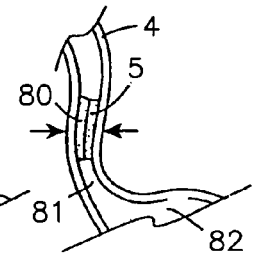
FIG. 10(e)  FIG. 10(f)  FIG. 10(g)  FIG. 10(h)
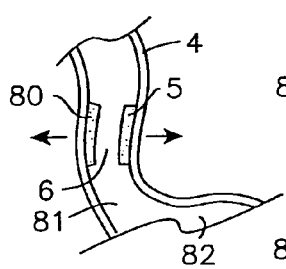 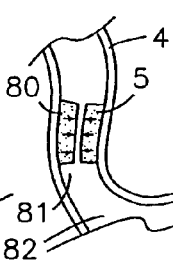 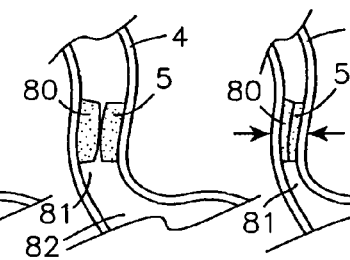 

FIG. 18   FIG. 19   FIG. 20   FIG. 21
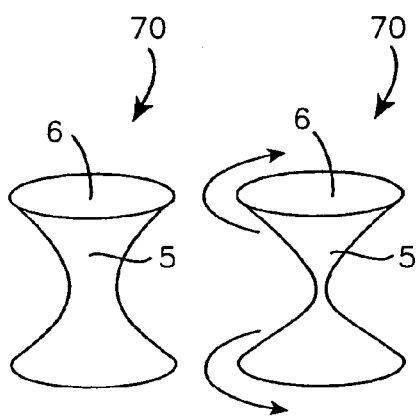
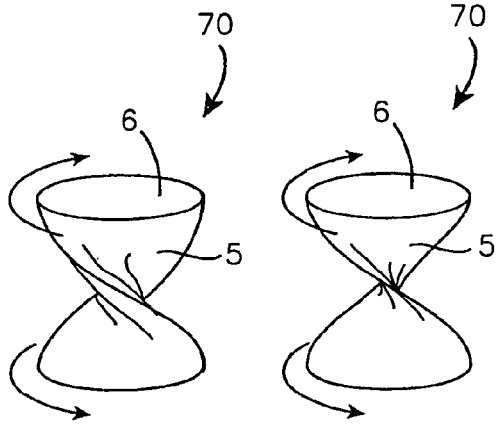
FIG. 22   FIG. 23   FIG. 24   FIG. 25
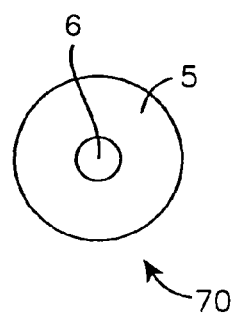
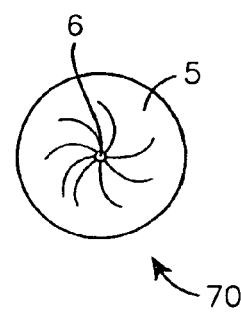
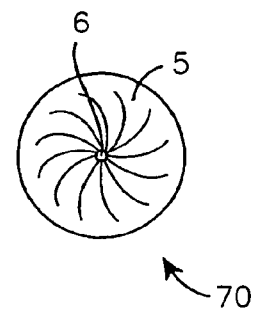

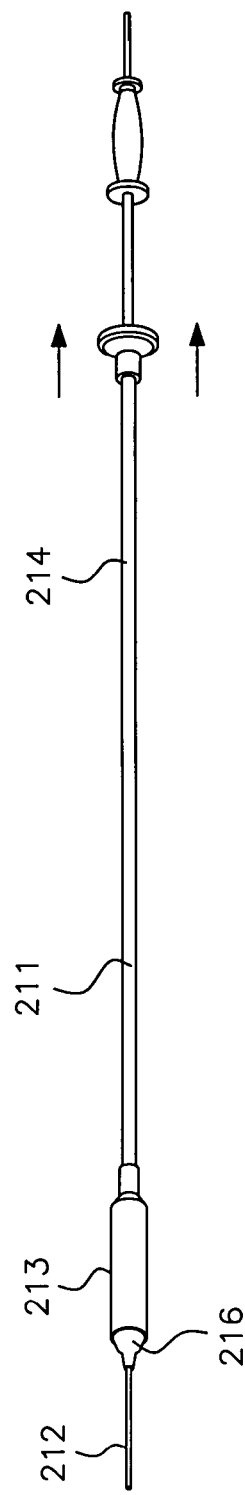
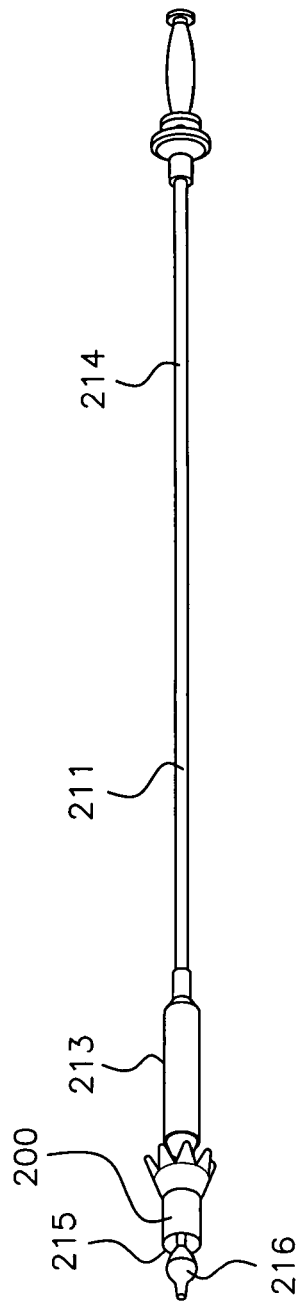
FIG. 39
FIG. 40

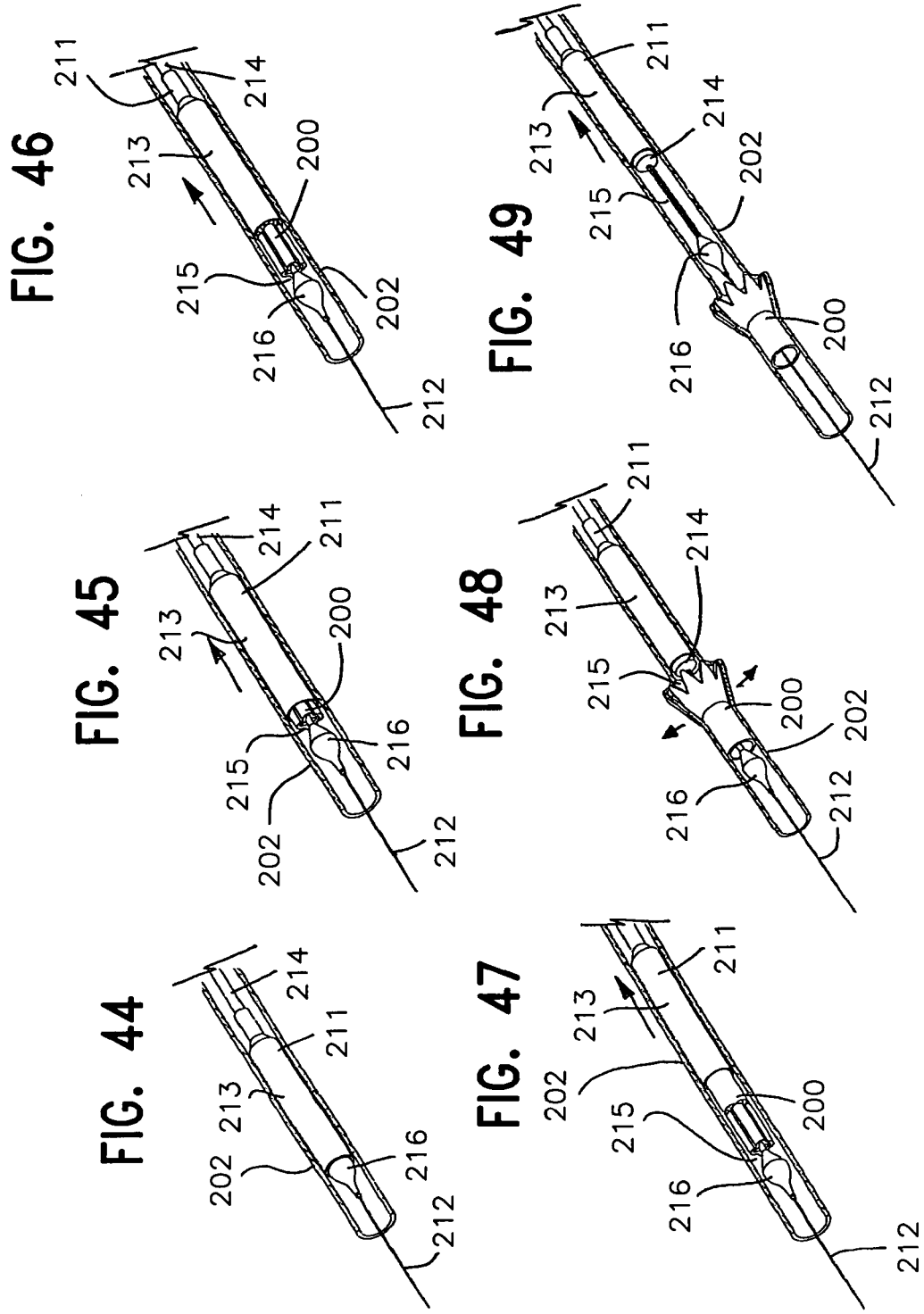

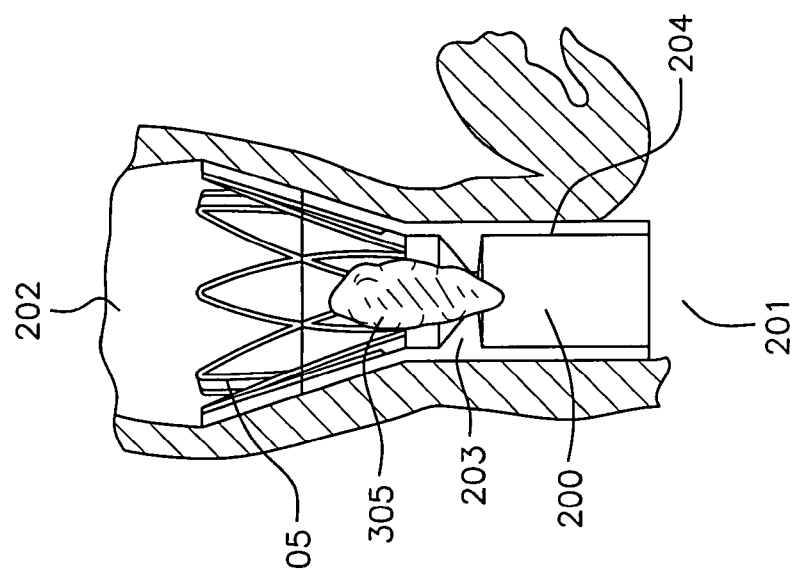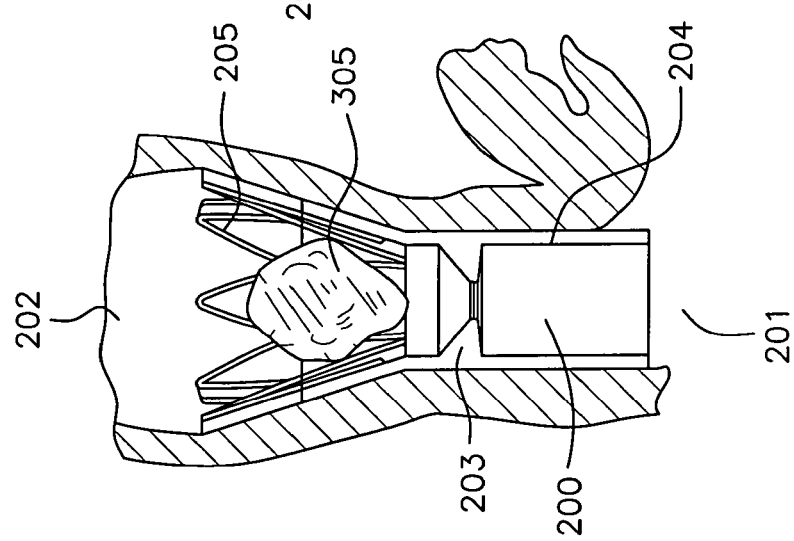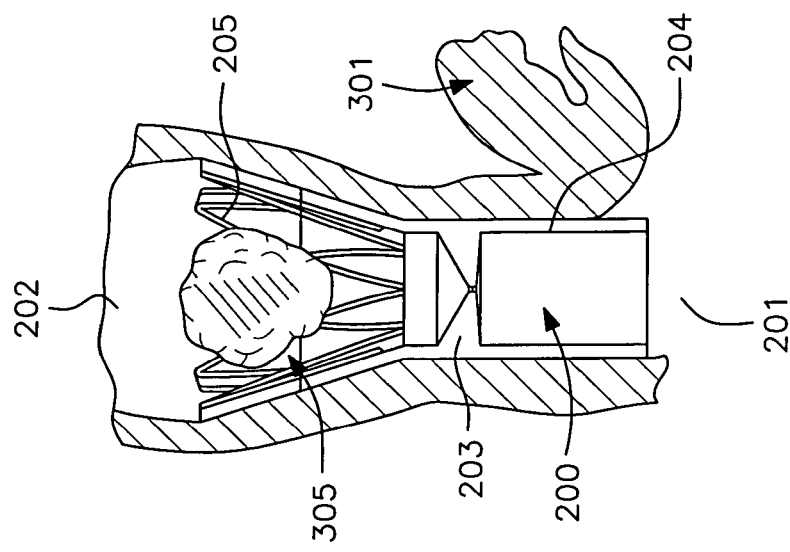

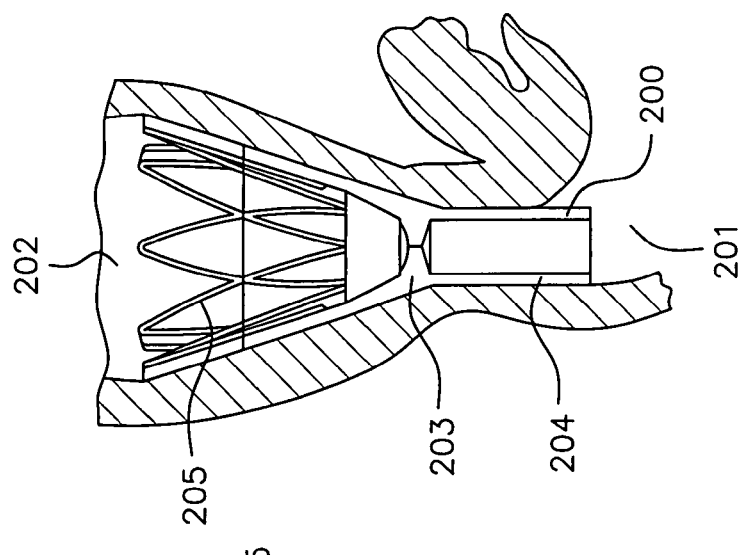
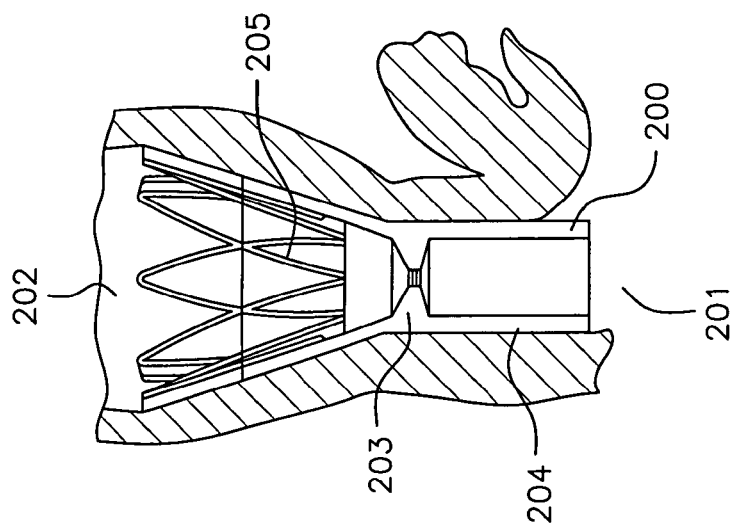
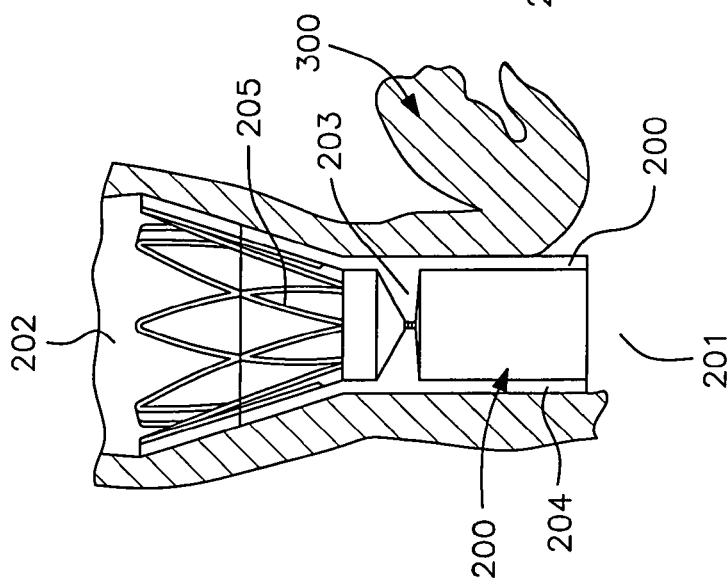

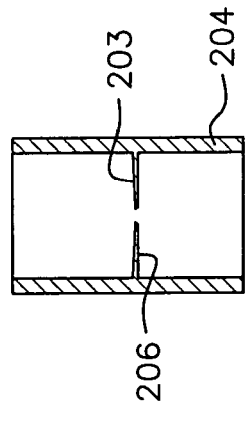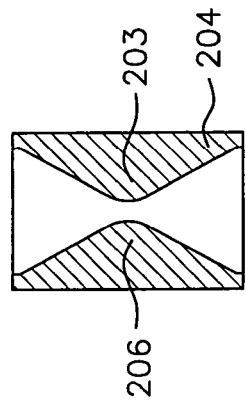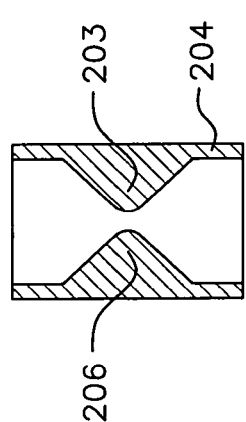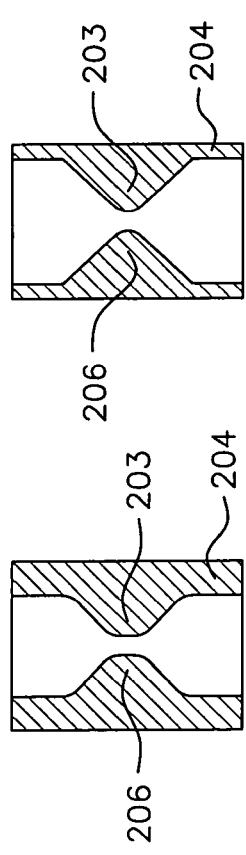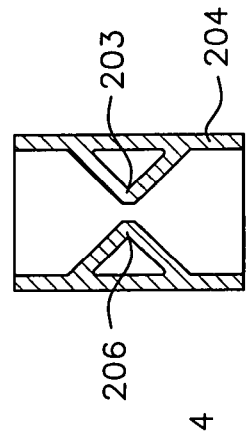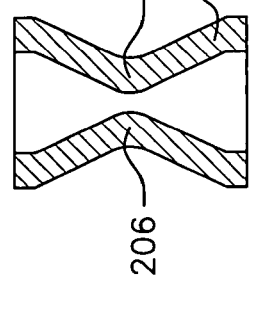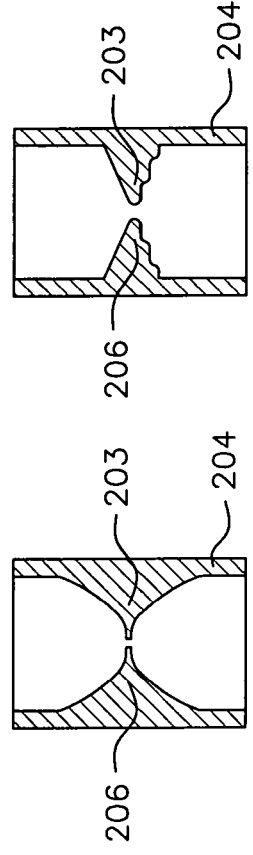
FIG. 61  FIG. 62  FIG. 63  FIG. 64  FIG. 65  FIG. 66  FIG. 67  FIG. 68

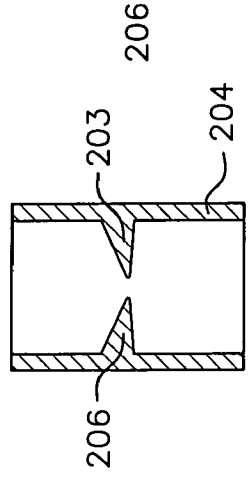
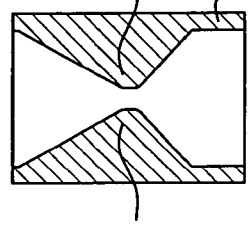
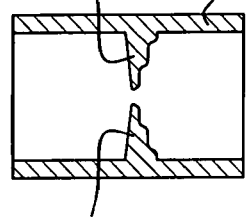
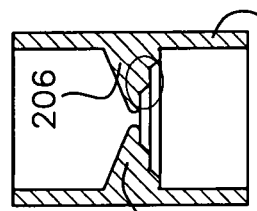
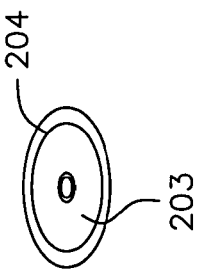
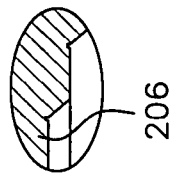

SECTION A-A

SECTION A-A

SECTION A-A

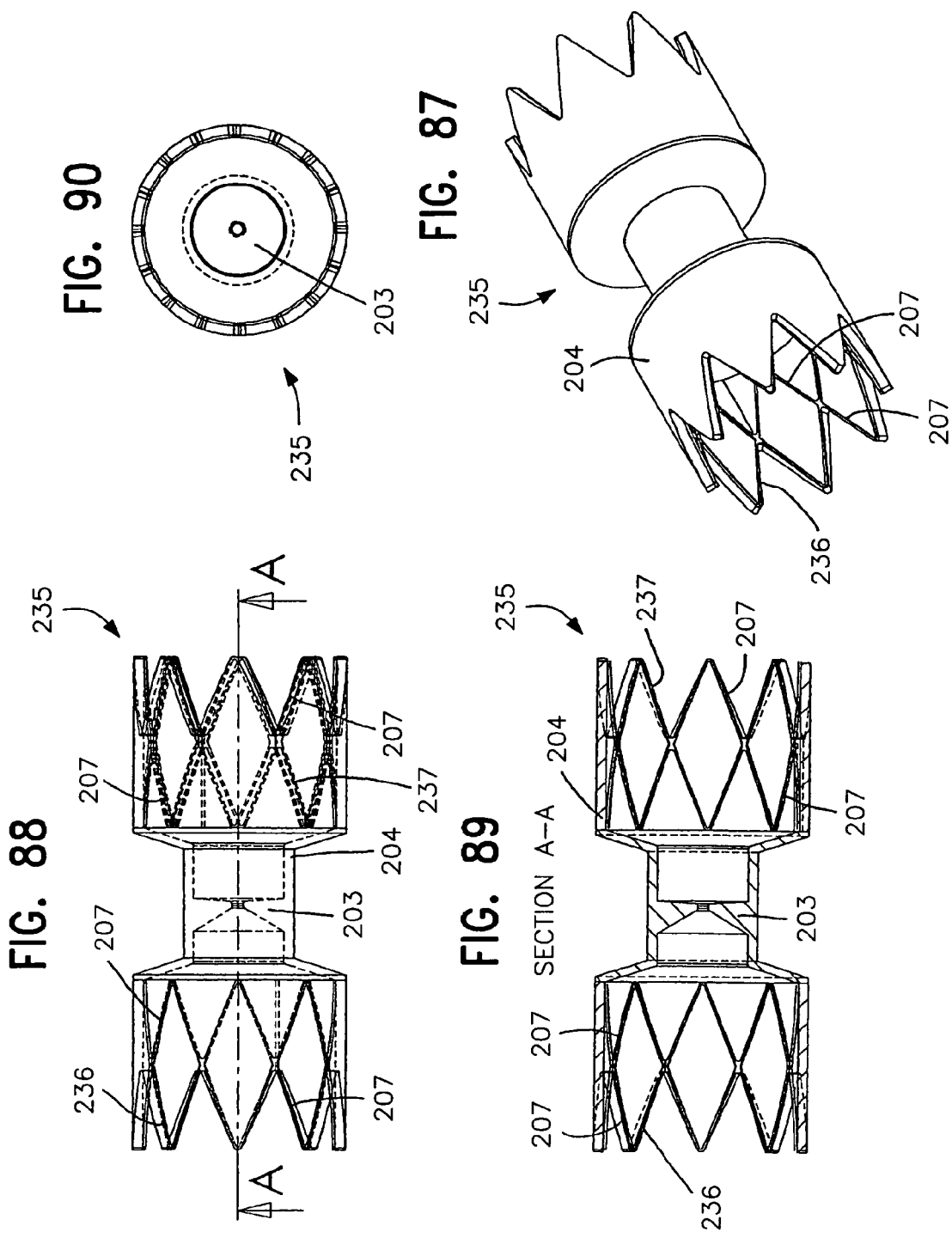

SECTION A-A

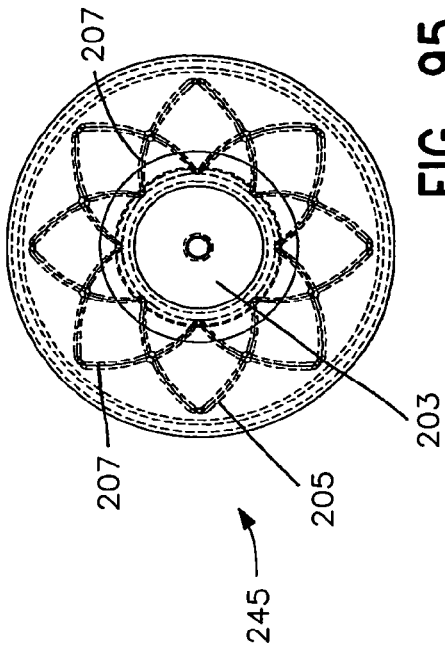
FIG. 98
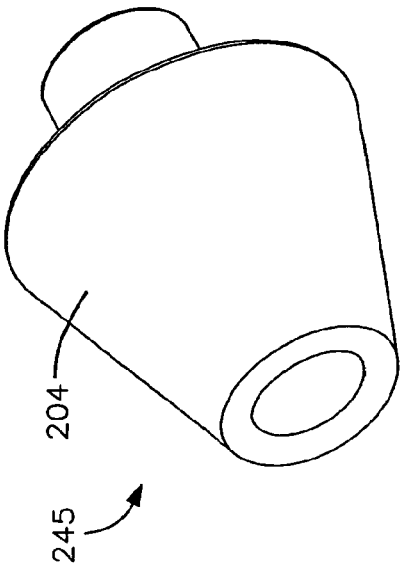
FIG. 95
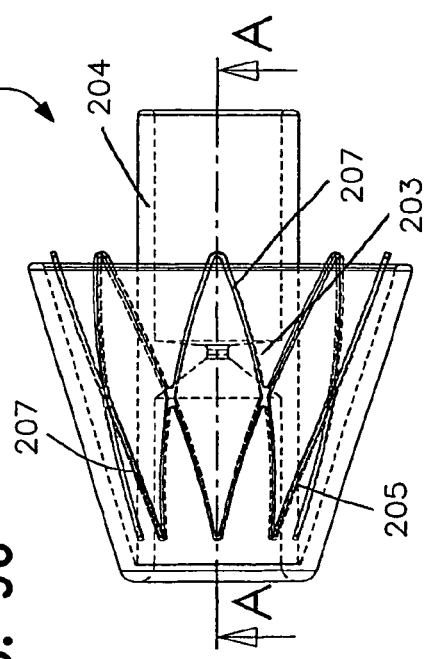
FIG. 96
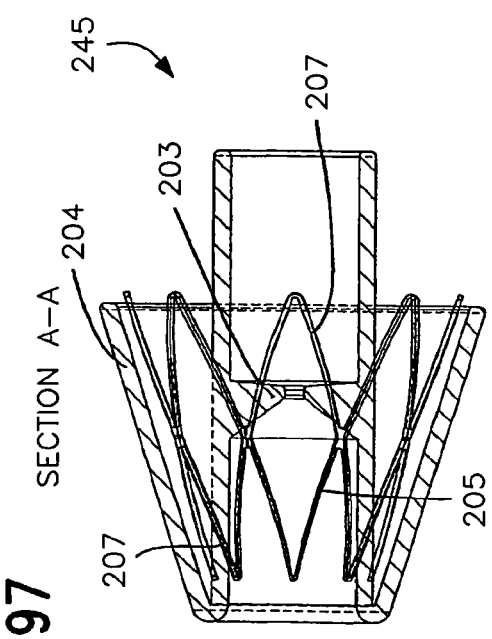
FIG. 97 SECTION A-A

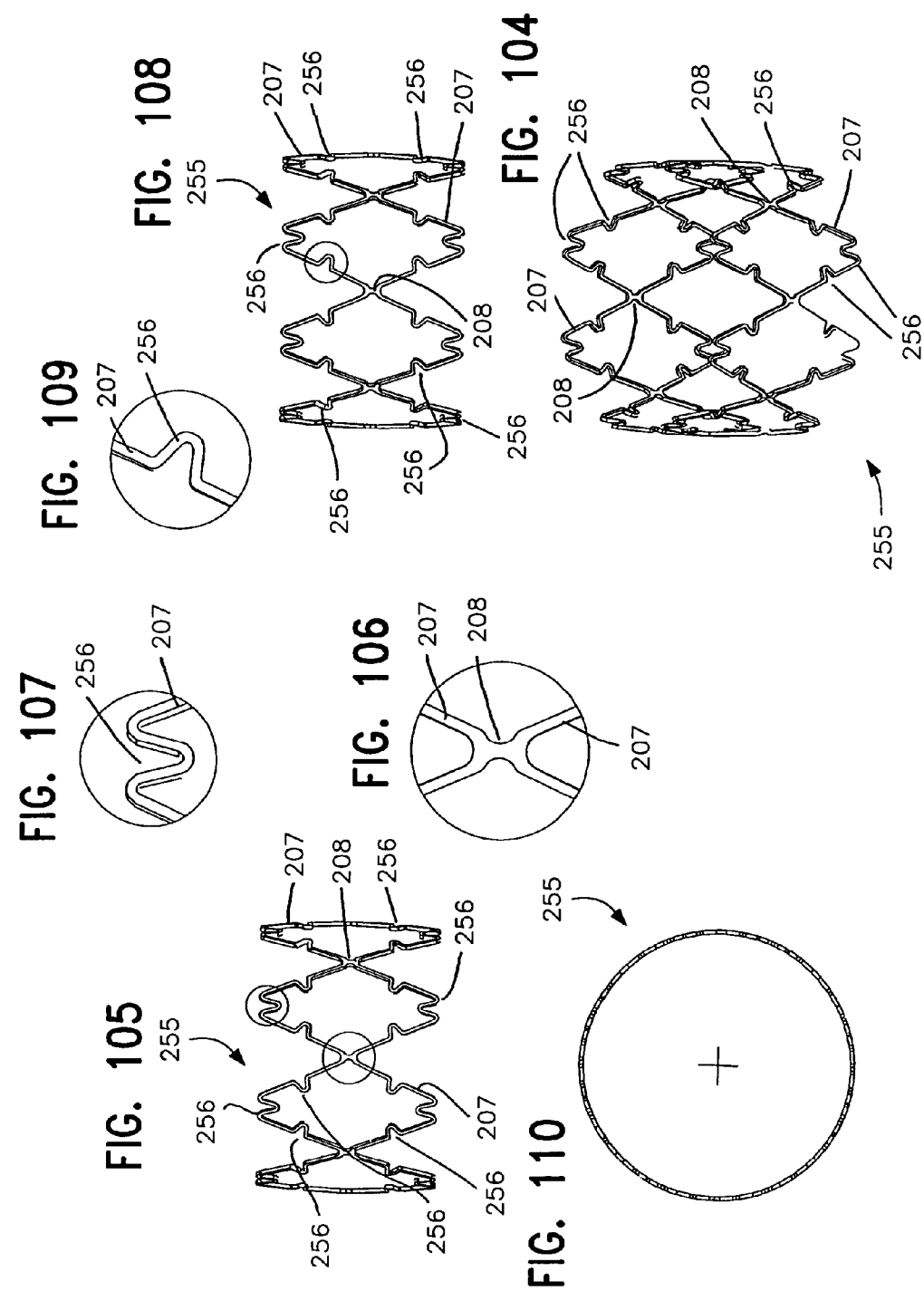

MEDICAL DEVICE SUITABLE FOR TREATING REFLUX FROM A STOMACH TO AN OESOPHAGUS

CROSS-REFERENCE TO RELATED APPLICATIONS

This application is a Continuation of U.S. patent application Ser. No. 11/643,698, filed Dec. 22, 2006, which claims priority to U.S. provisional patent application Ser. No. 60/752,881, filed Dec. 23, 2005, the entirety of each of which is hereby incorporated herein by reference.

This invention relates to a medical device suitable for treating reflux from a stomach to an oesophagus, to a medical device suitable for delivering a therapeutic agent to an alimentary canal, to a method of delivering a medical treatment device to a treatment location in an alimentary canal, and to a delivery system for delivering a medical treatment device to a treatment location in an alimentary canal.

STATEMENTS OF INVENTION

According to the invention there is provided a medical device suitable for treating reflux from a stomach to an oesophagus, the device comprising:—
  a valve member;
  the valve member being movable between an open configuration to facilitate passage of material between an oesophagus and a stomach, and a closed configuration;
  the valve member being configured to gradually move from the open configuration to the closed configuration over a predetermined period of time.

In the closed configuration the valve member fully prevents or substantially minimises any reflux from the stomach to the oesophagus.

The valve member moves gradually from the open configuration to the closed configuration. The valve member thus acts in a similar manner to the natural physiological action of the oesophageal sphincter.

In one embodiment of the invention in the open configuration the valve member is configured to facilitate passage of material from an oesophagus into a stomach. In the open configuration the valve member may be configured to facilitate passage of material from a stomach into an oesophagus. The valve member may facilitate swallowing of food from the oesophagus into the stomach, and may facilitate vomiting from the stomach into the oesophagus. Thus the valve member may act as a two-way valve. Preferably the device is biased towards the closed configuration. Ideally the valve member is configured to be moved from the closed configuration to the open configuration upon passage of material through the device.

In one case the period of time is greater than 1 secs. Preferably the period of time is at least 4 secs. Ideally the period of time is less than 20 secs. Most preferably the period of time is not greater than 10 secs. The period of time may be between 4 secs and 10 secs.

In one embodiment the valve member comprises a viscoelastic material. Preferably the valve member comprises a foam. Ideally the valve member comprises a polyurethane material.

In one case the valve member comprises one or more valve leaflets. Preferably the valve leaflet extends substantially radially inwardly. Ideally the valve leaflet is movable between a contracted configuration and an expanded configuration. Most preferably valve leaflet is in the contracted configuration when the valve member is in the open configuration. The valve leaflet may be in the expanded configuration when the valve member is in the closed configuration.

In another embodiment the valve member is located proximally of the distal end of the device. The valve member may be located distally of the proximal end of the device.

In another embodiment the device comprises at least one support member to support the device relative to an oesophagus and/or a stomach. Preferably the support member is located distally of the valve member. Ideally the support member is located proximally of the valve member. Most preferably the support member is arranged co-axially relative to the valve member. The support member may extend co-axially around the valve member.

In one case the device comprises a distal support member and a proximal support member. Preferably the proximal support member is larger than the distal support member. Ideally the radial dimension of the proximal support member is larger than the radial dimension of the distal support member.

The proximal support member may be substantially of equal size to the distal support member.

In one case the support member is tapered. Preferably the support member tapers distally radially inwardly.

The support member may taper distally radially outwardly.

The radial dimension of the support member may substantially constant along the support member.

In one embodiment the support member comprises two or more support elements. Preferably a first support element is coupled to a second support element. Ideally the region of coupling of the first support element to the second support element comprises an articulation region. Most preferably the support element comprises at least one articulation region intermediate a first coupling region and a second coupling region. The support element may extend circumferentially in a wave-pattern. The support element may extend circumferentially in a zig-zag pattern.

In one case the support member comprises a shape memory material. Preferably the support member comprises Nitinol. Ideally the support member comprises a stent.

In another case the support member is engagable with a wall of an oesophagus and/or a stomach. The support member may be extendable into a wall of an oesophagus and/or a stomach. Preferably the support member comprises at least one anchor element for anchoring the device to a wall of an oesophagus and/or a stomach. Ideally the anchor element comprises a pointed tip. The anchor element may be at least partially substantially frusto-conically shaped. The anchor element may be at least partially substantially bullet shaped.

In one case the support member comprises at least one support ring. Preferably the support member comprises a plurality of support rings spaced apart along the device. Ideally the support member comprises a first support ring at a first end of the device and a second support ring at a second end of the device.

In one embodiment the support member is configured to attach the lining device to an inner surface of an oesophagus and/or a stomach. Preferably the support member comprises an adhesive.

The device may comprise a lining member for lining a part of an inner surface of an oesophagus and or a stomach. Preferably the lining member is located radially outwardly of the valve member. Ideally the lining member is formed integrally with the valve member. Most preferably the lining member extends distally of the valve member.

The lining member may be located radially outwardly of the support member. Preferably the support member extends proximally of the lining member.

In one case the support member is provided external of the lining member. The support member may be engagable against an inner surface of the lining member. The support member may be at least partially embedded within the lining member. The support member may extend through the lining member.

In another case the device is configured to be located at least partially in an oesophagus.

The device may be configured to be located at least partially in a stomach.

In one embodiment the device is configured to line around the entire circumference of a part of an inner surface of an oesophagus and/or a stomach. Preferably the device is substantially tubular. Ideally the device defines a lumen therethrough. Most preferably at least part of the device is movable between an open configuration in which the lumen is open and a sealed configuration in which the lumen is closed. The device may be twistable between the open configuration and the sealed configuration. The device may be expandable from the open configuration to the sealed configuration.

In another case the radial dimension of the outer surface of the device is substantially constant along the device.

The radial dimension of the outer surface of the device may vary along the device. The outer surface of the device may taper inwardly from an end of the device towards the centre of the device. Preferably the outer surface of the device tapers inwardly from each end of the device towards the centre of the device.

The radial dimension of the inner surface of the device may vary along the device. The inner surface of the device may taper inwardly from an end of the device towards the centre of the device. Preferably the inner surface of the device tapers inwardly from an end of the device towards the centre of the device.

In another case the device comprises a sleeve.

The device may be configured to line around only part of the circumference of a part of an inner surface of an oesophagus and/or a stomach. Preferably the device comprises a patch and/or a prosthesis.

In one case the device is configured to deliver a pharmaceutical agent to an inner surface of an oesophagus and/or a stomach. Preferably the lining member is configured to deliver a pharmaceutical agent.

In another embodiment the device has a delivery configuration for delivery of the device to a deployment location, and a deployment configuration for deployment at the deployment location. Preferably the device is contracted in the delivery configuration. Ideally the device is expanded in the deployment configuration.

The device may be movable between a first deployment configuration and a second deployment configuration. Preferably the device is expandable from the first deployment configuration to the second deployment configuration. Ideally the device is contractable from the second deployment configuration to the first deployment configuration. Most preferably the device is biased towards the second deployment configuration. The device may be configured to move from the first deployment configuration to the second deployment configuration over a predetermined period of time. Preferably in the first deployment configuration, the device is configured to seal across an oesophagus with a lower oesophageal sphincter closed. Ideally in the second deployment configuration, the device is configured to seal across an oesophagus experiencing transient lower oesophageal sphincter relaxation.

The device may be at least partially of a polymeric material. The device may be at least partially of a viscoelastic foam. At least part of the device may be bioabsorbable. At least part of the device may be biodegradable.

The device may be configured to line a part of an inner surface of an oesophagus. The device may be configured to line a part of an inner surface of a stomach. The device may be configured to line a part of an inner surface of a colon.

In another aspect of the invention there is provided a medical device suitable for delivering a therapeutic agent to an alimentary canal, the device comprising:—
 a therapeutic agent delivery member;
 the delivery member comprising at least one pore;
 the delivery member defining a storage space for storing a therapeutic agent.

In one embodiment the delivery member is configured to be located in an alimentary canal in direct contact with an inner surface of the alimentary canal. Preferably the delivery member is a single layer member. Ideally the delivery member comprises a viscoelastic material. Most preferably the delivery member comprises a foam. The delivery member may comprise a polyurethane material. Preferably the delivery member comprises a cellular material.

The diameter of at least one of the cells may be in the range of from 0.5 µm to 1000 µm. Preferably the diameter of at least one of the cells is in the range of from 100 µm to 500 µm.

The storage space may be located in a strut of a cell. The width of the strut may be in the range of from 1 µm to 200 µm. Preferably the width of the strut is in the range of from 1 µm to 10 µm.

The density of the delivery member material may be in the range of from 10 kg/m$^3$ to 400 kg/m$^3$. Preferably the density of the delivery member material is in the range of from 50 kg/m$^3$ to 150 kg/m$^3$.

In another case the device comprises at least one support member to support the delivery member relative to an alimentary canal. Preferably the support member is configured to attach the delivery member to an inner surface of an alimentary canal. Ideally the support member comprises an adhesive.

In one case the support member is configured to support the delivery member lining a part of an inner surface of an alimentary canal. The support member may be provided external of the delivery member. The support member may be engagable against an inner surface of the delivery member. The support member may be at least partially embedded within the delivery member. The support member may extend through the delivery member.

In one case the support member is engagable with a wall of an alimentary canal. Preferably the support member is extendable into a wall of an alimentary canal. Ideally the support member comprises at least one anchor element for anchoring the delivery member to a wall of an alimentary canal. Most preferably the anchor element comprises a pointed tip. The anchor element may be at least partially substantially frusto-conically shaped. The anchor element may be at least partially substantially bullet shaped.

In one embodiment the support member comprises at least one support ring. Preferably the support member comprises a plurality of support rings spaced apart along the delivery member. Ideally the support member comprises a first support ring at a first end of the delivery member and a second support ring at a second end of the delivery member.

In another case the delivery member is configured to line around the entire circumference of a part of an inner surface of an alimentary canal. Preferably the delivery member is substantially tubular. Ideally the delivery member defines a lumen therethrough.

In another embodiment the radial dimension of the outer surface of the delivery member is substantially constant along the delivery member.

The radial dimension of the outer surface of the delivery member may vary along the delivery member. The outer surface of the delivery member may taper inwardly from an end of the delivery member towards the centre of the delivery member. Preferably the outer surface of the delivery member tapers inwardly from each end of the delivery member towards the centre of the delivery member.

The radial dimension of the inner surface of the delivery member may vary along the delivery member. The inner surface of the delivery member may taper inwardly from an end of the delivery member towards the centre of the delivery member. Preferably the inner surface of the delivery member tapers inwardly from each end of the delivery member towards the centre of the delivery member.

In one case the delivery member comprises a sleeve.

The delivery member may be configured to line around only part of the circumference of a part of an inner surface of an alimentary canal. Preferably the delivery member comprises a patch and/or a prosthesis.

In another case the device has a delivery configuration for delivery of the device through an alimentary canal to a deployment location, and a deployment configuration for deployment at the deployment location. Preferably the device is contracted in the delivery configuration. Ideally the device is expanded in the deployment configuration.

The delivery member may be at least partially of a polymeric material. At least part of the device may be bioabsorbable. At least part of the device may be biodegradable.

The device may be configured to deliver a therapeutic agent to a colon. The device may be for delivering a therapeutic agent to an inner surface of an alimentary canal. The device may be for delivering a therapeutic agent to an oesophagus. The device may be for delivering a therapeutic agent to a stomach.

In another aspect of the invention there is provided a method of delivering a medical treatment device to a treatment location in an alimentary canal, the method comprising the steps of:
    providing a medical treatment device;
    providing a delivery catheter;
    locating the medical treatment device at least partially within the delivery catheter;
    advancing the delivery catheter through an alimentary canal; and
    deploying the medical treatment device out of the delivery catheter at a treatment location in the alimentary canal In one embodiment the method comprises the step of collapsing at least part of the medical treatment device before locating at least partially within the delivery catheter. Preferably the medical treatment device is collapsed into a folded configuration. By collapsing the medical treatment device into the folded configuration, this provides for a low-profile when the medical treatment device is collapsed.

The medical treatment device may be located within the delivery catheter by drawing the medical treatment device at least partially into the delivery catheter. The medical treatment device may be located within the delivery catheter by advancing at least part of the delivery catheter relative to the medical treatment device.

In one case the method comprises the steps of:—
    providing a medical guidewire; and
    advancing the medical guidewire through the alimentary canal.

Preferably the delivery catheter is advanced over the medical guidewire. The medical guidewire may act as a guide path for the delivery of the delivery catheter through the alimentary canal.

The medical treatment device may be deployed by retracting at least part of the delivery catheter relative to the medical treatment device. The medical treatment device may be deployed by advancing at least part of the delivery catheter relative to the medical treatment device.

In one embodiment the medical treatment device expands after deployment out of the delivery catheter. Preferably the medical treatment device self-expands upon deployment out of the delivery catheter.

In another case the method comprises the steps of:—
    providing a deployment aid member; and
    locating the deployment aid member between the medical treatment device and the delivery catheter.

The deployment aid member may minimise frictional forces acting between the medical treatment device and the delivery catheter. In this way deployment of the medical treatment device out of the delivery catheter may be eased. Similarly loading of the medical treatment device into the delivery catheter may be eased.

Preferably the method comprises the step of deploying the deployment aid member out of the delivery catheter at the treatment location. Ideally the deployment aid member is deployed upon deployment of the medical treatment device.

In another embodiment the method comprises the step of, after deploying the medical treatment device out of the delivery catheter, locating the medical treatment device at least partially within the delivery catheter. By locating the medical treatment device within the delivery catheter for a second time, this enables the location of the medical treatment device to be moved or adjusted to a second treatment location. Preferably the method comprises the step of moving the delivery catheter through the alimentary canal. Ideally the method comprises the step of deploying the medical treatment device out of the delivery catheter at a second treatment location in the alimentary canal.

In one case the method comprises the step of withdrawing the delivery catheter from the alimentary canal.

The method may be a method of delivering a medical treatment device to a treatment location in an oesophagus.

The method may be a method of delivering a medical treatment device to a treatment location in a stomach.

The invention also provides in a further aspect a delivery system for delivering a medical treatment device to a treatment location in an alimentary canal, the system comprising:—
    a delivery catheter;
    the delivery catheter comprising a reception space into which a medical treatment device may by at least partially located.

In one embodiment the delivery catheter has a delivery configuration for delivery of a medical treatment device through an alimentary canal to a treatment location, and a deployment configuration for deployment of the medical treatment device at the treatment location.

The delivery catheter may comprise an outlet from the reception space through which a medical treatment device is passable for deployment of the medical treatment device. Preferably the delivery catheter comprises a shoulder adjacent to the outlet. Ideally the shoulder extends radially outwardly. Most preferably the shoulder extends around the circumference of the delivery catheter.

In one case at least part of the delivery catheter is retractable relative to a medical treatment device to deploy the medical treatment device out of the delivery catheter. Preferably the part of the delivery catheter comprises a sheath.

In another case at least part of the delivery catheter is advanceable relative to a medical treatment device to deploy the medical treatment device out of the delivery catheter. Preferably the part of the delivery catheter comprises a pusher.

The delivery catheter may comprise an ejector movable between the delivery configuration and the deployment configuration to deploy a medical treatment device out of the reception space.

The delivery catheter may comprise an expandable portion. Preferably a medical treatment device is mountable over the expandable portion. Ideally the expandable portion is contracted in the delivery configuration. The expandable portion may be expanded in the deployment configuration.

In one case the delivery catheter comprises a cover element. Preferably in the delivery configuration the cover element extends over a medical treatment device to cover the medical treatment device. Ideally in the delivery configuration the cover element restrains a medical treatment device. In the deployment configuration the cover element may be retracted to uncover a medical treatment device.

In another case the system comprises a deployment aid member for location between a medical treatment device and the delivery catheter. Preferably the deployment aid member is coupled to a medical treatment device. Ideally the deployment aid member comprises a low co-efficient of friction material. The deployment aid member may be substantially tubular. Preferably the deployment aid member comprises a sleeve. Ideally the deployment aid member comprises a biodegradable material.

In one case the system comprises a medical guidewire. Preferably the delivery catheter is advanceable over the medical guidewire.

The system may be a delivery system for delivering a medical treatment device to a treatment location in an oesophagus.

The system may be a delivery system for delivering a medical treatment device to a treatment location in a stomach.

In a further aspect of the invention there is provided a kit comprising:—
  a medical treatment device; and
  a delivery system for delivering the medical treatment device to a treatment location in an alimentary canal of the invention In one case the medical treatment device is movable between a collapsed configuration and an expanded configuration. Preferably the medical treatment device is substantially folded in the collapsed configuration. Ideally the medical treatment device is biased towards the expanded configuration.

The medical treatment device may comprise a device of the invention.

The medical treatment device of the invention solves the problems associated with one-way valves as it is designed to allow flow in both directions. In one embodiment the device does not actually occlude the oesophageal lumen completely but merely adds bulk around the sphincter to augment the natural function of the muscle. It may mechanically mimic the action of the native oesophageal tissue in that it compresses, distends and relaxes in a similar fashion, thus lending itself to function in a 'physiologically mimetic' fashion. Because the device is physiologically mimetic it does not need to invert or change orientation thus representing a significant improvement. The device may act as a prosthetic sphincter insert.

The invention provides a mechanism for the control of drug release from a biomaterial. The invention does not need to have multiple layers of material to control drug release.

The invention is not invasive and is not placed into tissue. Rather the invention is located on the surface of tissue.

The medical treatment device of the invention is not elastic, but rather mimics the characteristics of the native tissue. The device does not penetrate the oesophageal tissue and thus does not cause injury to the tissue.

According to another aspect of the invention there is provided a medical device comprising means for lining a part of an inner surface of an alimentary canal. By lining part of the inner surface of the alimentary canal, this enables the alimentary canal to be treated.

In one embodiment of the invention the device comprises means to support the lining means lining a part of an inner surface of an alimentary canal. By supporting the lining means, this assists in maintaining the lining means in the desired location and in resisting dislodgement of the lining means, for example due to peristaltic motion of the alimentary canal or to food passing through the alimentary canal. Preferably the support means comprises means to attach the lining means to an inner surface of an alimentary canal. Ideally the attachment means comprises an adhesive.

In one case the support means comprises a support element for supporting the lining means lining a part of an inner surface of an alimentary canal. Preferably the support element is provided external of the lining means. Ideally the support element is engagable against an inner surface of the lining means. The support element may be at least partially embedded within the lining means. The support element may extend through the lining means. The support element may be engagable with a wall of an alimentary canal. Preferably the support element is extendable into a wall of an alimentary canal. Ideally the support element comprises at least one anchor element for anchoring the lining means to a wall of an alimentary canal. Most preferably the anchor element comprises a pointed tip. The anchor element may be at least partially substantially frusto-conically shaped. The anchor element may be at least partially substantially bullet shaped.

In one embodiment the support element comprises at least one support ring. Preferably the support element comprises a plurality of support rings spaced apart along the lining means. Ideally the support element comprises a first support ring at a first end of the lining means and a second support ring at a second end of the lining means.

In another case the lining means is configured to line around the entire circumference of a part of an inner surface of an alimentary canal. Preferably the lining means is substantially tubular. Ideally the lining means defines a lumen therethrough. Most preferably at least part of the lining means is movable between an open configuration in which the lumen is open and a sealed configuration in which the lumen is closed. When the lining means is in the sealed configuration, the lumen is closed down. The medical device may therefore be employed as an artificial muscle, for example as an artificial sphincter, for example at the junction of the oesophagus and the stomach to prevent acid reflux from the stomach. The medical device may function as a mechanical device to replace the working of the original muscle. The lining means may be twistable between the open configuration and the sealed configuration. Preferably the lining means is expandable from the open configuration to the sealed configuration.

The radial dimension of the outer surface of the lining means may be substantially constant along the lining means. The radial dimension of the outer surface of the lining means may vary along the lining means. The outer surface of the lining means may taper inwardly from an end of the lining means towards the centre of the lining means. Preferably the outer surface of the lining means tapers inwardly from each end of the lining means towards the centre of the lining means.

The radial dimension of the inner surface of the lining means may vary along the lining means. Preferably the inner surface of the lining means tapers inwardly from an end of the lining means towards the centre of the lining means. Ideally the inner surface of the lining means tapers inwardly from each end of the lining means towards the centre of the lining means.

In another embodiment the lining means comprises a sleeve.

In one case the lining means is configured to line around only part of the circumference of a part of an inner surface of an alimentary canal. Preferably the lining means comprises a patch and/or a prosthesis.

In one embodiment the device comprises means to deliver a pharmaceutical agent to an inner surface of an alimentary canal. A function of the medical device may be to deliver pharmaceuticals to the inner surface or lining of the alimentary canal. By delivering the pharmaceutical agent to the inner surface of the alimentary canal, this arrangement enables focussed, localised drug delivery to be achieved to optimise treatment and minimise any undesirable side-effects of the pharmaceutical agent. Preferably the lining means comprises the means to deliver the pharmaceutical agent.

In another case the lining means has a delivery configuration for delivery of the lining means through an alimentary canal to a deployment location and a deployment configuration for deployment at the deployment location. In the delivery configuration, the lining means may have a low-profile configuration for ease of navigation through the alimentary canal. Preferably the lining means is contracted in the delivery configuration. Ideally the lining means is expanded in the deployment configuration.

In one embodiment the lining means is movable between a first deployment configuration and a second deployment configuration. Preferably the lining means is expandable from the first deployment configuration to the second deployment configuration. Ideally the lining means is contactable from the second deployment configuration to the first deployment configuration. Most preferably the lining means is biased towards the second deployment configuration. The lining means may be configured to move from the first deployment configuration to the second deployment configuration upon elapse of a predetermined period of time. Preferably in the first deployment configuration, the lining means is configured to seal across an oesophagus with a lower oesophageal sphincter closed. Ideally in the second deployment configuration, the lining means is configured to seal across an oesophagus experiencing transient lower oesophageal sphincter relaxation.

The lining means may be at least partially of a polymeric material. The lining means may be at least partially of a viscoelastic foam. At least part of the device may be bioabsorbable. At least part of the device may be biodegradable.

The lining means may be configured to line a part of an inner surface of an oesophagus. The lining means may be configured to line a part of an inner surface of a stomach. The lining means may be configured to line a part of an inner surface of a colon.

In another aspect the invention provides a delivery device for delivering a medical device to a deployment location in an alimentary canal, the device having a delivery configuration for delivery of the medical device through the alimentary canal to the deployment location, and a deployment configuration for deployment of the medical device at the deployment location. In the delivery configuration, the delivery device may have a low-profile configuration for ease of navigation through the alimentary canal.

In one embodiment in the delivery configuration the device comprises a reception space for receiving a medical device. Preferably the device comprises an outlet from the reception space through which a medical device is passable for deployment of the medical device. Ideally the device comprises a shoulder adjacent to the outlet. The shoulder of the delivery device acts to push the walls of the alimentary canal outwardly to ease deployment of the medical device. Most preferably the shoulder extends radially outwardly. The shoulder may extend around the circumference of the device.

In one case the device comprises an ejector movable between the delivery configuration and the deployment configuration to deploy a medical device out of the reception space.

The device may comprise an expandable portion. Preferably a medical device is mountable over the expandable portion. Ideally the expandable portion in contracted in the delivery configuration. Most preferably the expandable portion is expanded in the deployment configuration.

The device may comprise a cover element. Preferably in the delivery configuration the cover element extends over a medical device to cover the medical device. Ideally in the delivery configuration the cover restrains a medical device. Most preferably in the deployment configuration the cover element is retracted to uncover a medical device.

In one case the device is configured to deliver a medical device to a deployment location in an oesophagus. The device may be configured to deliver a medical device to a deployment location in a stomach. The device may be configured to deliver a medical device to a deployment location in a colon.

The invention also provides in a further aspect a kit comprising:—
  a medical device of the invention; and
  a delivery device for delivering the medical device to a deployment location in an alimentary canal.

In one embodiment the delivery device comprises a device of the invention.

According to another aspect of the invention there is provided a method of treating an alimentary canal comprising the step of lining a part of an inner surface of the alimentary canal.

In one embodiment a lining means is supported lining part of the inner surface of the alimentary canal. Preferably the lining means is attached to the inner surface of the alimentary canal.

The method may comprise the step of engaging a support element with a wall of the alimentary canal. Preferably the support element is extended into the wall of the alimentary canal. Ideally the lining means is anchored to the wall of the alimentary canal.

In one case the lining means is moved between an open configuration in which a lumen through the lining means is open, and a sealed configuration in which the lumen is closed.

In another embodiment the method comprises the step of delivering a pharmaceutical agent to the inner surface of the alimentary canal.

The method may comprise the step of delivering the lining means through the alimentary canal to a deployment location. Preferably the method comprises the step of deploying the lining means at the deployment location to line part of the inner surface of the alimentary canal. Ideally the lining means is deployed by expanding the lining means. Most preferably the lining means is deployed by passing the lining means out of a reception space of a delivery device. The lining means may be deployed by retracting a cover element of a delivery device to uncover the lining means.

In one case the invention provides a method of treating an oesophagus. The invention may provide a method of treating an oesophagus experiencing transient lower oesophageal sphincter relaxation.

In another case the invention provides a method of treating a stomach.

The invention may provide a method of treating a colon.

A function of the medical device may be for wound healing. The invention may provide a means of protecting injured gastric tissue for weeks or months to enable healing.

The invention may provide a system for applying an endoluminal gastric coating.

The invention may provide a device, which is introduced into the gastrointestinal tract using an endoscope. The device may incorporate a means of placing a soft polymeric covering or lining onto the gastrointestinal surface or epithelium. The covering or lining may be made from an adhesive gel type material, such as hydrogel, silicone, chitosan gel or alginate gel, or polyurethane foams. The covering or lining may comprise an overlayer that prevents displacement of the prosthesis due to digestive processes. The overlayer may be a polymeric film or a metal spring clip. The polymeric covering or lining may be loaded with a drug to treat a specific underlying disease state, such as an ulcer, tumour or surgery induced scar. The prosthesis may be tailored to degrade over a preset period of time facilitating its removal from the body.

The invention may provide a device designed to be attached to an endoscope for treatment of gastrointestinal diseases. The device may have a degradable adhesive polymer prosthesis, and a mechanism for attachment of the prosthesis to the gastric mucosa. The prosthesis may contain a pharmaceutical compound for localised drug delivery.

BRIEF DESCRIPTION OF THE DRAWINGS

The invention will be more clearly understood from the following description of some embodiments thereof, given by way of example only, with reference to the accompanying drawings, in which:—

FIG. 6 is a partially cut-away, isometric view of another medical device according to the invention, in use;

FIG. 10(a) is a cross-sectional, side view of another medical device according to the invention deployed in an alimentary canal;

FIGS. 10(b) to 10(h) are cross-sectional, side views of the medical device of FIG. 10(a), in use;

FIGS. 18 to 21 are isometric views of a further medical device according to the invention, in use;

FIGS. 22 to 25 are plan views corresponding to FIGS. 18 to 21 respectively of the medical device;

FIGS. 39 and 40 are isometric views of the delivery catheter of FIG. 35 and the device of FIG. 26, in use;

FIGS. 44 to 49 are isometric views of the delivery catheter of FIG. 35 and the device of FIG. 26, in use;

FIGS. 50 to 54 are cross-sectional, side views of the device of FIG. 26, in use;

FIGS. 55 to 60 are further cross-sectional, side views of the device of FIG. 26, in use;

FIGS. 61 to 72 are cross-sectional, side views of other medical treatment devices according to the invention;

FIG. 73 is an enlarged, cross-sectional, side view of a part of the device of FIG. 72;

FIG. 74 is a plan view of the device of FIG. 72;

FIGS. 87 to 90 are views similar to FIGS. 75 to 78 of another medical treatment device according to the invention;

FIGS. 95 to 98 are views similar to FIGS. 75 to 78 of a further medical treatment device according to the invention;

FIGS. 104 to 107 and 110 are views similar to FIGS. 99 to 103 of a support member of a further medical treatment device according to the invention;

FIG. 108 is another side view of the support member of FIG. 104; and

FIG. 109 is an enlarged, side view of a part of the support member of FIG. 108.

DETAILED DESCRIPTION

Figure 1:
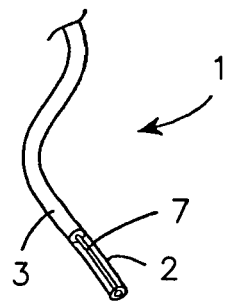
FIG. 1 is an isometric view of a medical device according to the invention mounted to a delivery device according to the invention.

Referring to the drawings, and initially to FIGS. 26 to 60 thereof, there is illustrated a medical treatment device 200 according to the invention. The device 200 is suitable for treating reflux from a stomach 201 to an oesophagus 202. The device 200 is also suitable for delivering a therapeutic agent to an inner surface of an alimentary canal, for example to the oesophagus 202 and/or to the stomach 201.

The device 200 comprises a valve member 203, a lining member 204 for lining part of the inner surface of the oesophagus 202 and/or the stomach 201, and a proximal support member 205 to support the device 200 relative to the oesophagus 202 and the stomach 201.

The valve member 203 is located proximally of the distal end of the device 200, and distally of the proximal end of the device 200.

The valve member 203 is movable between a closed configuration (FIG. 50) and an open configuration (FIG. 52). In the open configuration, the valve member 203 facilitates passage of material, such as food, from the oesophagus 202 into the stomach 201, and facilitates passage of material, such as vomit, from the stomach 201 into the oesophagus 202.

The valve member 203 comprises two valve leaflets 206 extending radially inwardly. The valve leaflets 206 are movable between an expanded configuration (FIG. 50) and a contracted configuration (FIG. 52). When the valve member 203 is in the closed configuration, the valve leaflets 206 are in the expanded configuration (FIG. 50). When the valve member 203 is in the open configuration, the valve leaflets 206 are in the contracted configuration (FIG. 52).

The valve member 203 may be moved from the closed configuration (FIG. 50) to the open configuration (FIG. 52) by passage of material, such as food, through the device 200. In particular, the food is forced through the oesophagus 202 by means of peristalsis. When the food reaches the valve member 203, the food engages the valve leaflets 206 and compresses the valve leaflets 206 from the expanded configuration to the contracted configuration. The food then passes through the open valve member 203 into the stomach 201.

Figure 53:
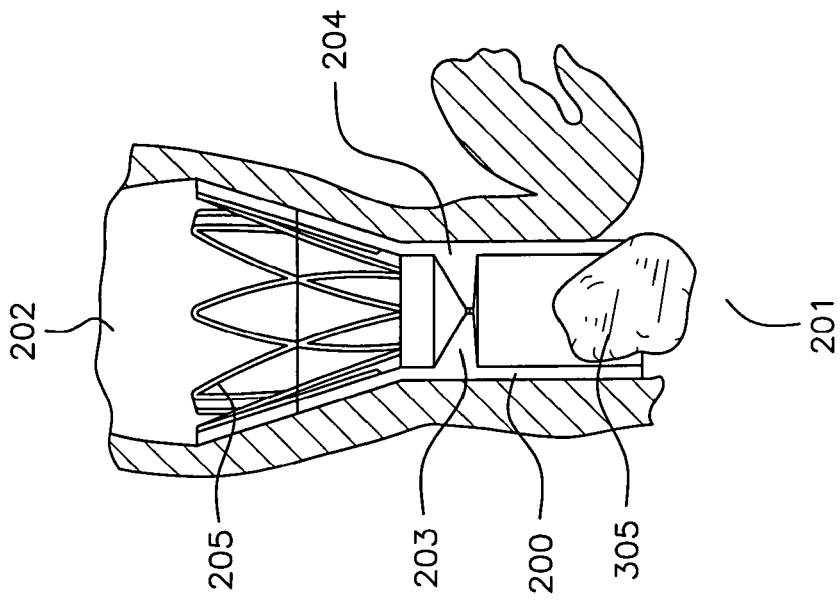
Figure 54:
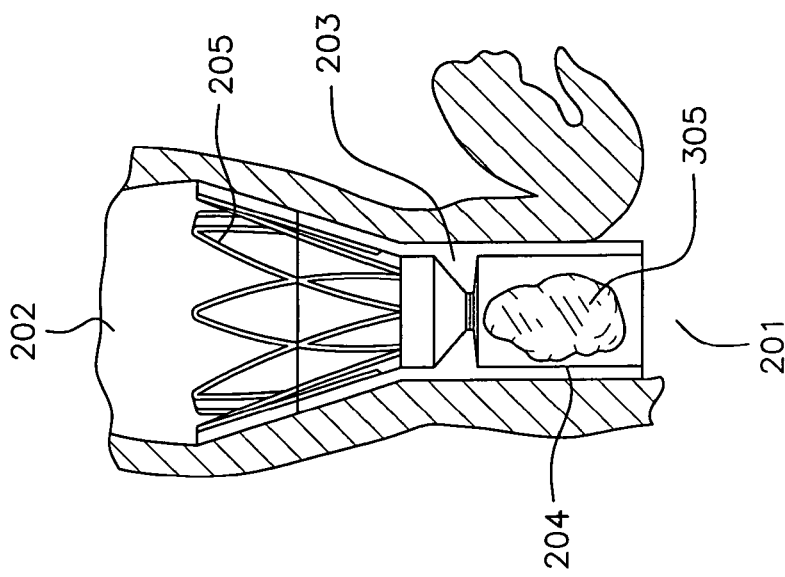

The valve member 203 is of a viscoelastic, polyurethane foam material. The valve member 203 is biased towards the closed configuration. However because of the viscoelastic nature of the valve member 203, the valve leaflets 206 do not move immediately from the contracted configuration to the expanded configuration. Rather, after the food has passed through the valve member 203, the valve leaflets 206 gradually move over a period of 4 to 10 seconds from the contracted configuration to the expanded configuration, as illustrated in FIGS. 52 to 54. Thus the valve member 203 gradually moves from the open configuration to the closed configuration over a period of 4 to 10 seconds.

The material of the valve member 203 may have the following characteristics:

the material may be viscoelastic;
the material may be a biomaterial;
the material may have shape memory;
the material may be a cellular material;
the material may be open cell or closed cell;
the material may have gas voids incorporated;
the material may be hydrolytically and oxidatively stable;
the material may be biomimetic;
the material may be biocompatible;
the material may be biostable;
the material may be a polymer.

The support member 205 is located proximally of the valve member 203.

The support member 205 tapers distally radially inwardly. In this manner the support member 205 acts as a funnel to guide material, such as food, from the oesophagus 202 towards the valve member 203.

As illustrated in FIGS. 27 to 30, the support member 205 is provided in the form of a stent. In particular the support member 205 comprises two support elements 207.

Each support element 207 extends circumferentially in a zig-zag, wave pattern. The support elements 207 are coupled to one another. Each region of coupling of the two support elements 207 to one another acts as an articulation region 208 (FIG. 29).

Each support element 207 is of a shape memory material, such as Nitinol.

Figure 29:
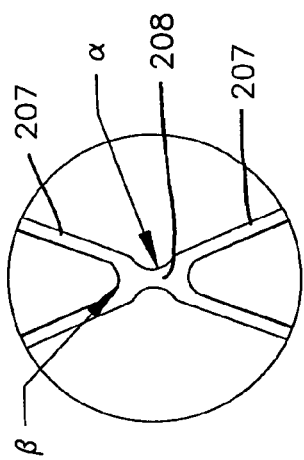
FIG. 29 is an enlarged, side view of a part of the support member of FIG. 28.
Figure 28:
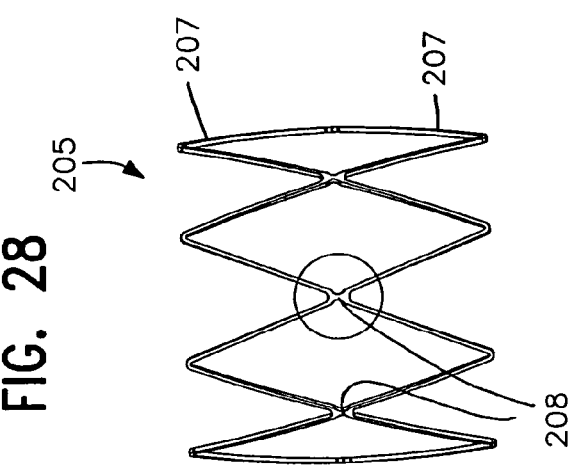
FIG. 28 is a side view of the support member of FIG. 27.
Figure 30:
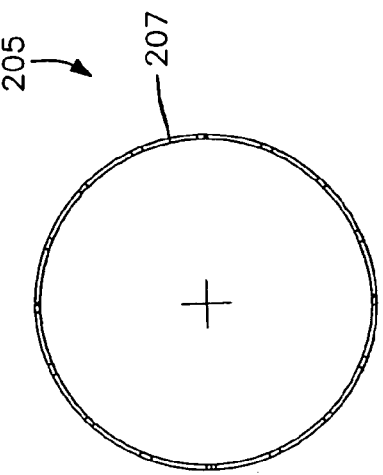
FIG. 30 is a plan view of the support member of FIG. 27.

FIGS. 27 to 30 illustrate the retention mechanism with a single articulation. FIG. 29 illustrates the articulation feature.

The angle α may be in the range of from 170° to 70°. The radius of curvature at this angle α may be in the range of from 0.9 mm to 0.1 mm.

The angle β may be in the range of from 95° to 5°. The radius of curvature at this angle β may be in the range of from 0.9 mm to 0.1 mm.

The lining member 204 is formed integrally with the valve member 203. The lining member 204 is located radially outwardly of the valve member 203 and extends distally of the valve member 203 in a substantially cylindrical tube shape. The lining member 204 is located radially outwardly of the support member 205 and extends proximally of the valve member 203. In this case the lining member 204 terminates at the proximal end of the support member 205.

When the device 200 is deployed, the lining member 204 is in direct contact with the inner surface of the oesophagus 202/stomach 201. The lining member 204 may be employed for delivery of a therapeutic agent to the oesophagus 202/stomach 201. In particular the lining member 204 comprises a single layer of a viscoelastic, polyurethane foam material. This material is a cellular material and comprises a plurality of pores. A therapeutic agent 209 may be stored in the struts 210 of the cells. The therapeutic agent 209 may also be stored in the pores, however the struts 209 are the primary location for storing the therapeutic agent 209. FIG. 32(a) illustrates the cellular structure of the foam.

The size of the cells may vary, for example the diameter of the cells may be in the range of from 0.5 μm to 1000 μm, preferably in the range of from 100 μm to 500 μm. Similarly the size of the structure may vary, for example the width of the struts 210 may be in the range of from 1 μm to 200 μm, preferably in the range of from 1 μm to 10 μm. Furthermore the density of the material may vary, for example the density of the material may be in the range of from 10 kg/m$^3$ to 400 kg/m$^3$, preferably in the range of from 50 kg/m$^3$ to 150 kg/m$^3$.

The material of the lining member 204 may have the following characteristics:
- the material may be viscoelastic;
- the material may be a biomaterial;
- the material may have shape memory;
- the material may be a cellular material;
- the material may be open cell or closed cell;
- the material may have gas voids incorporated;
- the material may be hydrolytically and oxidatively stable;
- the material may be biomimetic;
- the material may be biocompatible;
- the material may be biostable;
- the material may be a polymer.

Drug delivery to the inner lumen of the alimentary canal is a technical challenge for a number of reasons. The alimentary canal is a dynamic muscular structure that functions very efficiently to propel occluding items such as food through its length. Also, much of the tissue in the alimentary canal exhibits viscoelastic behaviour. This causes the tissue to relax slowly in response to an expansion caused by the passage of food. This makes it difficult to maintain a drug delivery system in contact with the endothelium for prolonged periods. Furthermore, the upper part of the alimentary canal, especially the oesophagus is poorly perfused relative to other areas of the body. This makes the systemic delivery of drugs to target the oesophageal tissue an inefficient means of achieving the correct bio-distribution.

The invention achieves drug delivery through the endothelium of the oesophagus by topical administration, i.e. applied directly to a part of the body. The invention maintains uninterrupted intimate contact with the endothelium, for the required duration of treatment. The invention carries sufficient quantity of the therapeutic agent, and delivers this at a rate appropriate to the indication being treated.

The medical treatment device of the invention has mechanical properties similar to the oesophagus. This ensures that there are no periods of endothelial non-contact and thus no interrupted drug release. The invention matches the viscoelastic/mechanical properties of the tissue in order to ensure uninterrupted dosage.

In the case where it is necessary to deliver a drug to a site close to a dysfunctional sphincter, the invention enables drug delivery from the outer surface of the anti-reflux valve to be used.

The medical treatment device of the invention may comprise a structure made from a material that mimics the mechanical properties of the gastrointestinal tract. The viscoelastic behaviour of this structure enables constant contact without the need for adhesive attachment. The medical treatment device of the invention may be a cellular foam, the structure and geometry of which may be altered to present a variety of surface areas available for direct contact.

Figure 31:
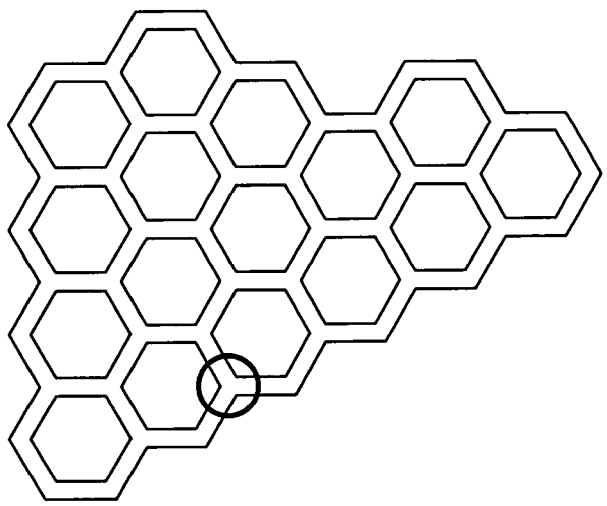
FIG. 31 is a schematic illustration of the material of the device of FIG. 26.

The rate of drug release may be controlled through variation of cellular structure. The surface area may be used as a means of achieving the optimum drug release kinetics. This approach has the additional benefit that diffusion control layers and the like are no longer necessary. The drug will be situated within the cell struts 210 as illustrated in FIGS. 31 and 32 and thus the dimensions of these struts 210 and the concentration of drug contained therein will influence the kinetic release properties.

Figure 32:
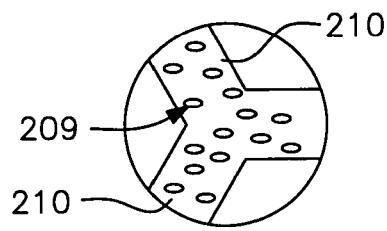
FIG. 32 is an enlarged, schematic illustration of the material of FIG. 31.
Figure 33:
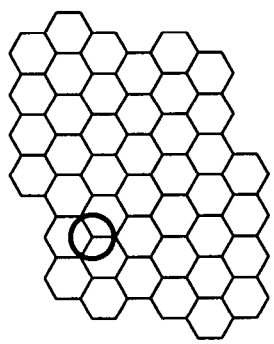
FIGS. 33 and 34 are views similar to FIGS. 31 and 32 of the material of another medical treatment device according to the invention.
Figure 34:
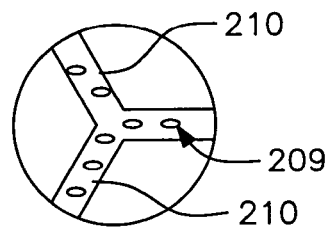
Figure 32A:
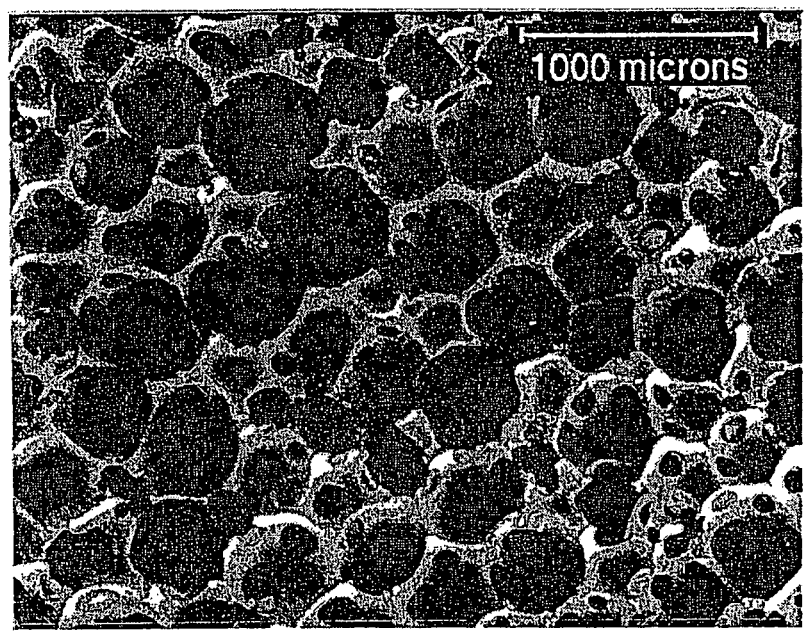
FIG. 32(a) is a photographic representation of the material of FIG. 31.
Figure 35:
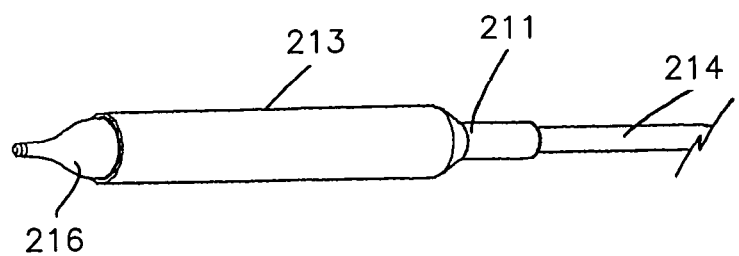
FIG. 35 is an isometric view of a delivery catheter of a delivery system according to the invention.
Figure 36:
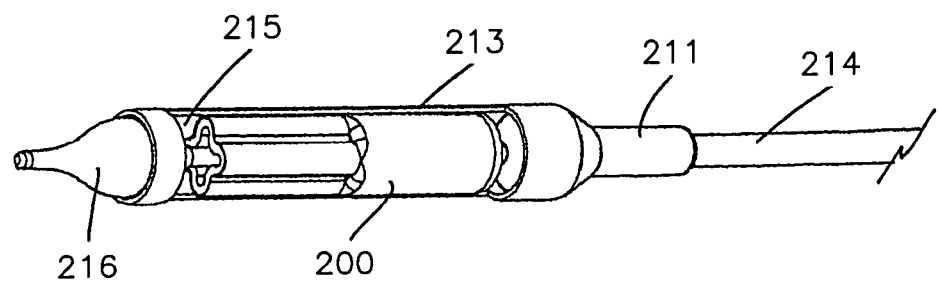
FIG. 36 is a partially cut-away, isometric view of the delivery catheter of FIG. 35 and the device of FIG. 26.

FIGS. 31 to 34 are schematic representations of drug molecules in foams with struts 210 of different dimensions. FIG. 32 illustrates the large cell struts 210 with greater drug loading and the drug molecules 209. FIG. 34 illustrates the small cell struts 210 with lower drug loading.

The foam cells may be between 0.5 and 1000 μm in diameter but ideally between 100 and 500 μm in diameter. The width of the struts 210 (or walls) of the cells may be between 1 μm and 200 μm but more preferably between 1 μm and 10 μm.

The density of the foam may be between 10 Kg/M$^3$ and 400 Kg/M$^3$ but more preferably between 50 Kg/M$^3$ and 150 Kg/M$^3$.

The compression and hysteresis behaviour of the foam material may be similar to that of human oesophageal tissue.

The medical treatment device of the invention may be used to deliver a variety of therapeutic agents including low molecular weight drugs such as H2 receptor antagonists, proton pump inhibitors or high molecular weight drugs such as proteins and peptides. In addition gene and cell based therapies may be delivered. Exemplary non-genetic therapeutic agents include anti-neoplastic/anti-proliferative/anti-mitotic agents such as paclitaxel, epothilone, cladribine, 5-fluorouracil, methotrexate, doxorubicin, daunorubicin, cyclosporine, cisplatin, vinblastine, vincristine, epothilones, endostatin, trapidil, halofuginone, and angiostatin; anti-cancer agents such as antisense inhibitors of c-myc oncogene; anti-microbial agents such as triclosan, cephalosporins, aminoglycosides, nitrofurantoin, silver ions, compounds, or salts; biofilm synthesis inhibitors such as non-steroidal anti-inflammatory agents and chelating agents such as ethylenediaminetetraacetic acid, O,O'-bis(2-aminoethypethyleneglycol-N,N,N'N'-tetraacetic acid and mixtures thereof; antibiotics such as gentamycin, rifampin, minocyclin, and ciprofolxacin; antibodies including chimeric antibodies and antibody fragments; anesthetic agents such as lidocaine, bupivacaine, and ropivacaine; nitric oxide; nitric oxide (NO) donors such as lisidomine, molsidomine, L-arginine, NO-carbohydrate adducts, polymeric or oligomeric NO adducts; and any combinations and prodrugs of the above.

Exemplary biomolecules include peptides, polypeptides and proteins; oligonucleotides; nucleic acids such as double or single stranded DNA (including naked and cDNA), RNA, antisense nucleic acids such as antisense DNA and RNA, small interfering RNA (siRNA), and ribozymes; genes; carbohydrates; angiogenic factors including growth factors; cell cycle inhibitors. Nucleic acids may be incorporated into delivery systems such as, for example, vectors (including viral vectors), plasmids or liposomes.

Exemplary small molecules include hormones, nucleotides, amino acids, sugars, and lipids and compounds have a molecular weights of less than 100 kD.

Exemplary cells include stem cells, progenitor cells, endothelial cells, adult cardiomyocytes, and smooth muscle cells. Cells can be of human origin (autologous or allogenic) or from an animal source (xenogenic), or genetically engineered. Non-limiting examples of cells include mesenchymal stem cells including mesenchymal stem cells with 5-aza, cord blood cells, endothelial progenitor progenitor cells, skeletal myoblasts or satellite cells, muscle derived cells, go cells, endothelial cells, genetically modified cells, tissue engineered grafts, embryonic stem cell clones, embryonic stem cells, fetal or neonatal cells, immunologically masked cells, and teratoma derived cells.

Figure 26:
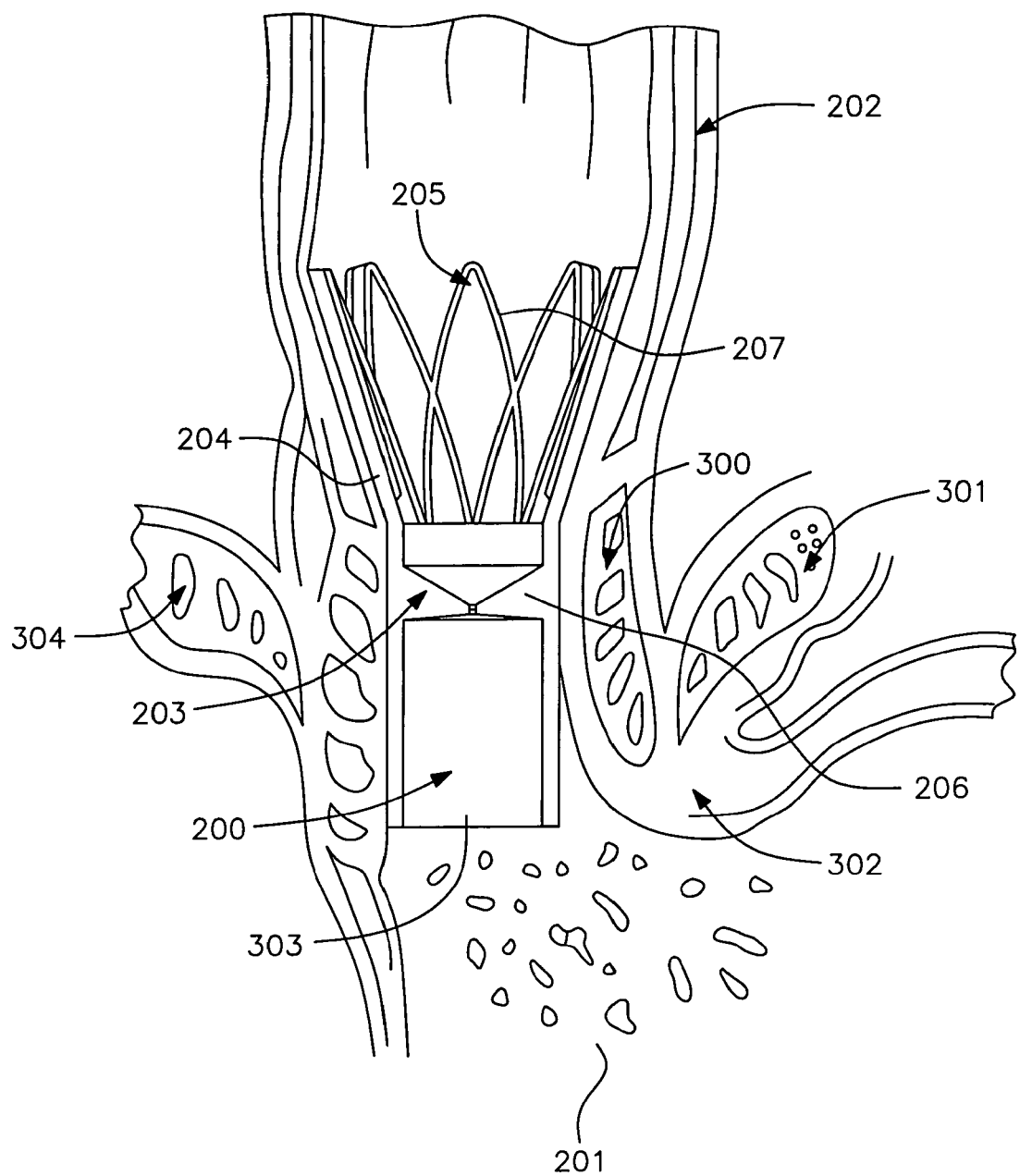
FIG. 26 is a cross-sectional, side view of a medical treatment device according to the invention.
Figure 27:
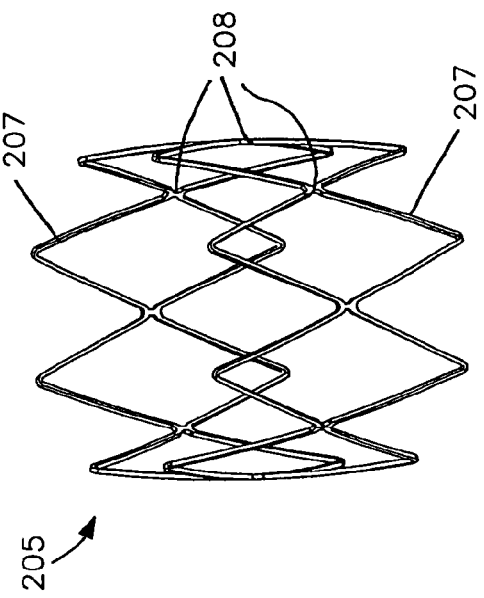
FIG. 27 is an isometric view of a support member of the device of FIG. 26.

FIG. 26 illustrates the reflux device 200 positioned at the lower oesophageal sphincter. FIG. 26 illustrates the esophagus 202, lower esophageal sphincter (LES) 300, crural diaphram 301, angle of His 302, anti-reflux device lumen 303, anti-reflux device barrier 203, crural diaphram 304, retention mechanism 205.

The length of the support member 205 is less than the wavelength of peristalsis. The typical peristalsis wavelength at the proximal oesophagus is 4.9 cm, at the mid oesophagus is 8.8 cm, and at the distal oesophagus is 6.8 cm.

In FIGS. 35 to 49 there is illustrated a delivery system according to the invention. The delivery system is suitable for delivering the device 200 to a treatment location in the alimentary canal, for example in the oesophagus 202 or in the stomach 201.

The delivery system comprises a delivery catheter 211, a medical guidewire 212, and a tubular sleeve 400 of a low co-efficient of friction material.

The delivery catheter 211 comprises a restraining sheath 213 and an elagate body element 214. The sheath 213 is movable relative to the body element 214 between a delivery configuration (FIG. 39) for delivery of the device 200 through the oesophagus 202 to the treatment location, and a deployment configuration (FIG. 40) for deployment of the device 200 at the treatment location. In the delivery configuration, the delivery catheter 211 defines a reception space 215 into which the device 200 is located. In the deployment configuration, the sheath 213 is retracted relative to the body element 214 to facilitate deployment of the device 200 out of the reception space 215.

The device 200 is movable between a collapsed, folded configuration (FIG. 37) and an expanded configuration (FIG. 40). The device 200 is located in the reception space 215 in the collapsed configuration. The device 200 is biased towards the expanded configuration.

The distal tip 216 of the body element 214 tapers proximally radially outwardly to provide a smooth crossing profile at the distal end of the delivery catheter 211.

The delivery catheter 211 may be advanced through the oesophagus 202 over the guidewire 212.

Figure 37:
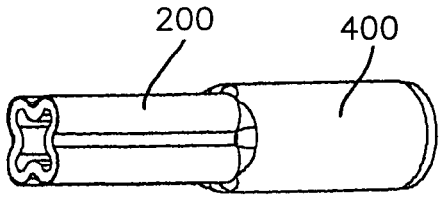
FIG. 37 is an isometric view of the device of FIG. 36.

The low-friction sleeve 400 is coupled to the device 200 (FIG. 37). When the device 200 is located in the reception space 215, the low-friction sleeve 400 is located between the device 200 and the internal wall of the sheath 213. Because of the low co-efficient of friction material, the low-friction sleeve 400 acts as an aid to ease deployment of the device 200 from the reception space 215, and also act as an aid to ease loading of the device 200 into the reception space 215.

The sleeve 400 is a biodegradable material.

Figure 38:
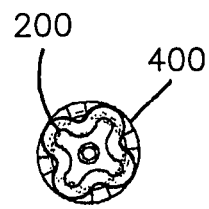
FIG. 38 is an end view of the device of FIG. 37.

FIGS. 35 to 38 illustrate:
anti-reflux device delivery system with tapered tip 216 and overtube 213 arrangement (FIG. 35)
interior detail of how anti-reflux device 200 is stored in folded/pleated configuration (FIG. 36)
detail of anti-reflux device 200 folding pattern (FIG. 37)
alginate or other biodegradable polymer wrapper (FIG. 38).

FIG. 37 is an isometric view of the crimped device 200.

FIGS. 39 and 40 are isometric illustrations showing the mechanism of the device deployment whereby an outer tube transfers a force to the distal end of the system thus retracting the overtube 213 and releasing the device 200 which quickly takes its native shape. FIGS. 39 and 40 are isometric views of deployment.

Figure 41:
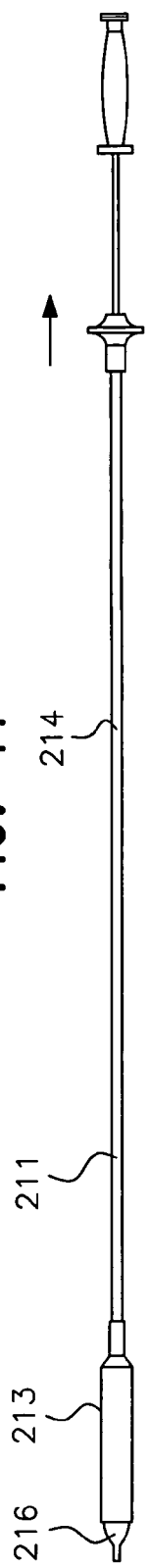
FIGS. 41 to 43 are side views of the delivery catheter of FIG. 35 and the device of FIG. 26, in use.
Figure 42:
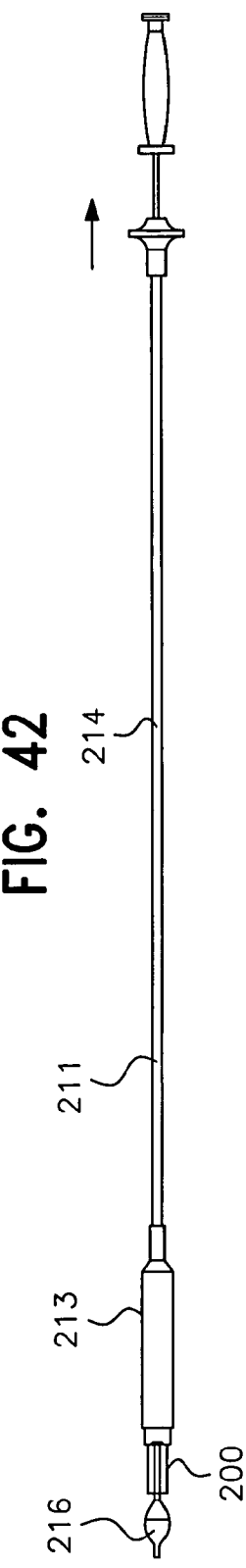
Figure 43:
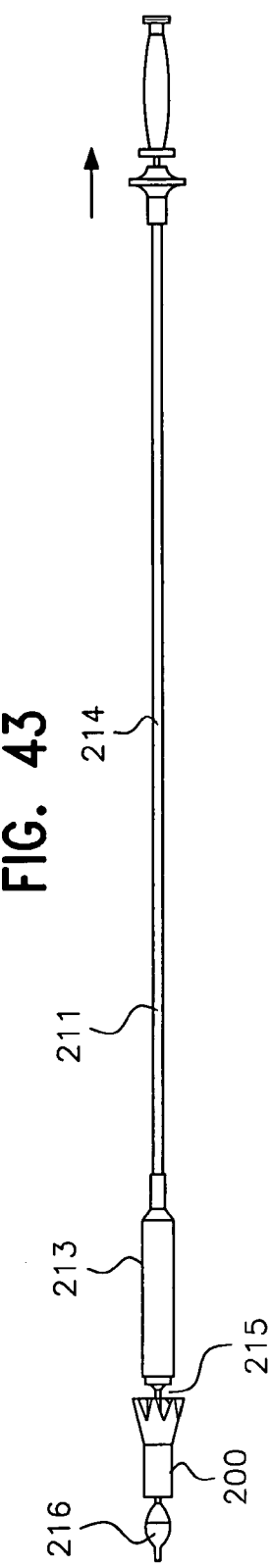

FIGS. 41 to 43 illustrate:
delivery system fully loaded (FIG. 41)
overtube 213 partially retracted from over anti-reflux device 200 revealing pleated/folded configuration (FIG. 42)
overtube 213 fully retracted from over anti-reflux device 200 with device 200 fully deployed (FIG. 43).

FIGS. 41 to 43 are elevation views of deployment.

FIGS. 44 to 49 illustrate:
delivery catheter 211 placed in the oesophagus 202 with a guidewire 212 running through a central lumen of the delivery system (FIG. 44).
overtube 213 retracting from over anti-reflux device 200 revealing pleated/folded configuration (FIGS. 45 to 47).
anti-reflux device 200 deployed into the oesophagus 202 with retention mechanism 205 engaging with inner lumen and endothelium (FIG. 48).
device 200 deployed and delivery system being retracted with tapered tip 216 passing through the centre of the anti-reflux device barrier 203 (FIG. 49).

FIGS. 44 to 49 are isometric views of the device 200 being deployed in situ.

In use, the device 200 is collapsed to the folded configuration (FIG. 37). The device 200, with the low-friction sleeve coupled thereto, is located in the reception space 215. The sheath 213 is advanced relative to the body element 214 over the collapsed device 200 to restrain the device 200. The low-friction sleeve acts to minimise frictional forces during advancement of the sheath 213 over the device 200.

The guidewire 212 is advanced through the oesophagus 202 until the distal end of the guidewire 212 is within the stomach 201. The delivery catheter 211 in the delivery configuration is advanced over the guidewire 212 until the collapsed device 200 is at the desired treatment location, for example at the oesophageal sphincter (FIG. 44).

The sheath 213 is then retracted while maintaining the position of the body element 214 substantially fixed (FIGS. 45 to 47). In this manner the device 200 is uncovered. The device 200 self-expands to the expanded configuration engaging the inner wall of the oesophagus 202 (FIG. 48). Part of the device 200 is located in the oesophagus 202 and part of the device 200 extends into the stomach 201. The delivery catheter 211 may then be withdrawn from the oesophagus 202 leaving the device 200 in the desired treatment location (FIG. 49).

The low-friction sleeve is deployed out of the reception space 215 upon deployment of the device 200. Over time the sleeve biodegrades.

FIGS. 50 to 54 illustrate the device 200 in use in the case where the oesophageal sphincter fails to close effectively to prevent reflux from the stomach 201 to the oesophagus 202. When the valve member 203 is in the closed configuration, reflux from the stomach 201 to the oesophagus 202 is prevented (FIG. 50). As food passes through the oesophagus 202 and into the device 200, the food forces the valve leaflets 206 to the contracted configuration (FIG. 52). When the valve member 203 is in the open configuration, the food may pass through the valve member 203 into the stomach 201. After the food has passed through the valve member 203, the valve leaflets 206 gradually move to the closed configuration (FIG. 54).

FIGS. 50 to 54 illustrate the reflux device 200 positioned at a dysfunctional LES 300 that does not close completely, and passage of a food bolus 305 through the reflux device 200 at the dysfunctional LES 300.

LES muscle 300 is dysfunctional and does not close normally—device 200 in anti-reflux configuration (FIG. 50).

Patient chews and swallows bolus of food 305 (FIG. 51).

Bolus 305 is propelled through the oesophagus 202 via peristalsis and is pushed through the anti-reflux barrier 203, which deforms readily (FIG. 52). Device anti-reflux barrier 203 relaxes gradually so as to assume anti-reflux configuration (FIG. 53).

Food bolus 305 has passed and device 200 maintains anti-reflux protection (FIG. 54).

The device 200 is also suitable for use in the case where the oesophageal sphincter opens erratically, or for relatively long periods of time, e.g. greater than 10 seconds, or when there is no food passing through the oesophagus 202 into the stomach 201, as illustrated in FIGS. 59 to 60. When the oesophageal sphincter opens (FIGS. 55 and 56), the valve leaflets 206 expand gradually and thus the valve member 203 gradually closes (FIG. 57). The valve member 203 remains in this closed configuration preventing reflux from the stomach 201 into the oesophagus 202, until the oesophageal sphincter begins to close again (FIG. 59). When the oesophageal sphincter closes fully, the valve leaflets 206 are contracted (FIG. 60). However reflux from the stomach 201 to the oesophagus 202 is still prevented.

FIGS. 55 to 60 illustrate the reflux device 200 positioned at the functioning LES 300 during opening/closing of the muscle.

LES muscle 300 open (either normally or inappropriately)—device 200 in anti-reflux configuration (FIG. 58).

LES 300 begins to close normally—device anti-reflux barrier 203 begins to compress (FIG. 59).

LES 300 closed—device anti-reflux barrier 203 completely collapsed to allow muscle closure (FIG. 60).

Figure 55:
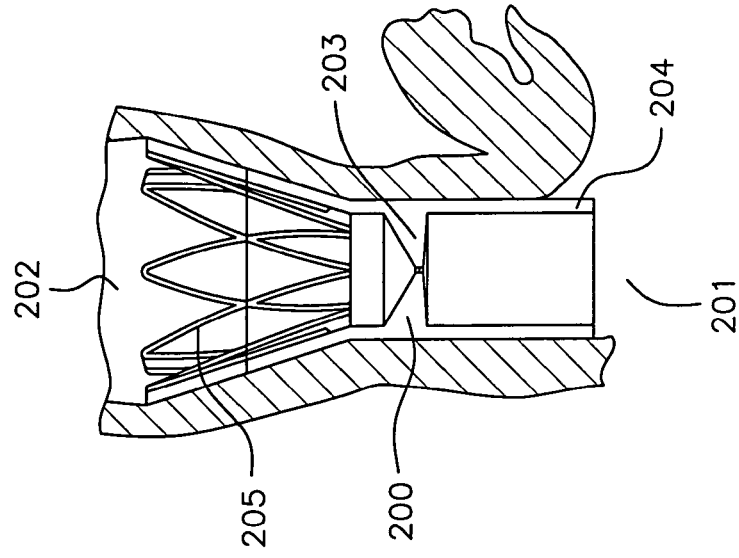

LES 300 begins to open—anti-reflux barrier 203 stays compressed (FIG. 55).

Figure 56:
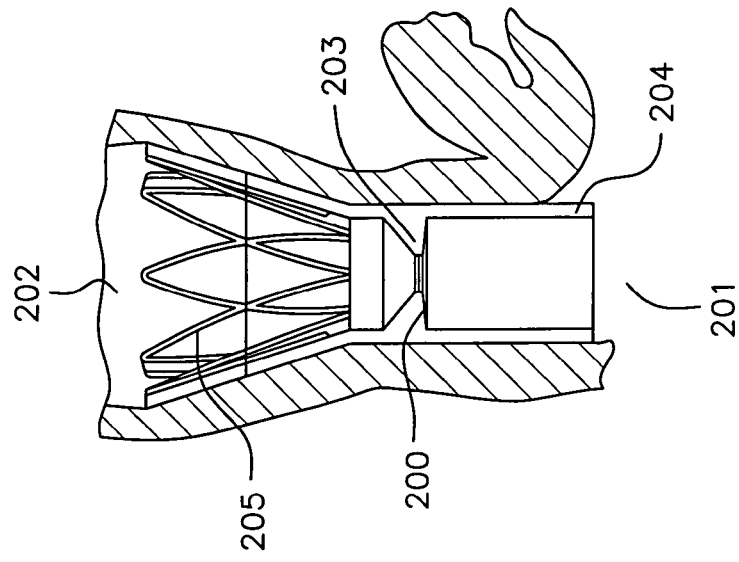
Figure 57:
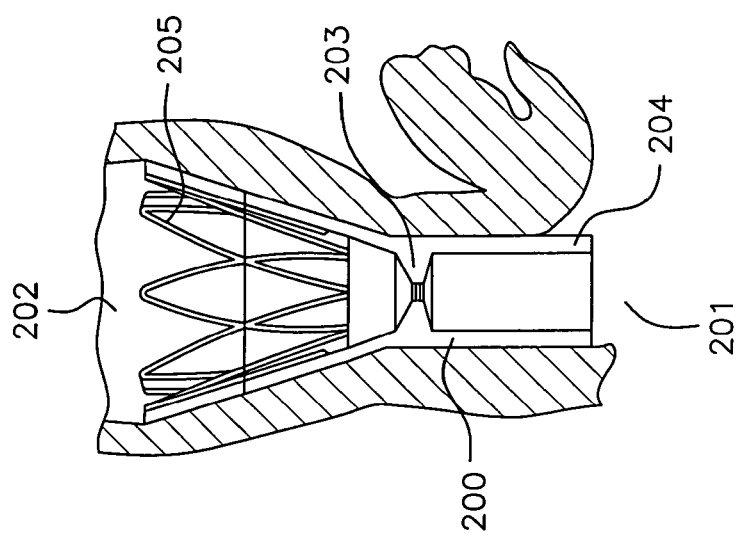
Figure 78:
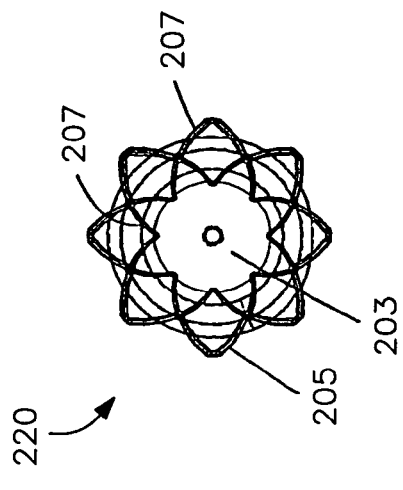
FIG. 78 is a plan view of the device of FIG. 75.
Figure 75:
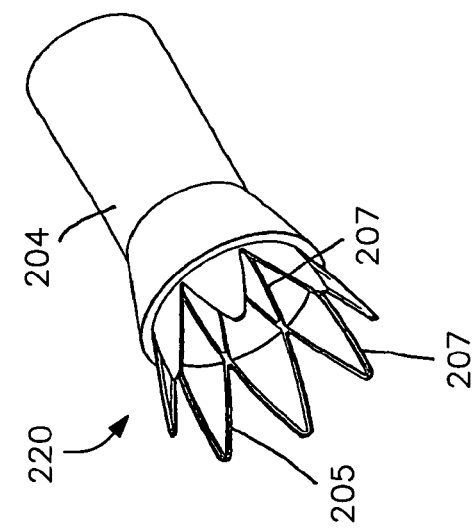
FIG. 75 is an isometric view of another medical treatment device according to the invention.
Figure 76:
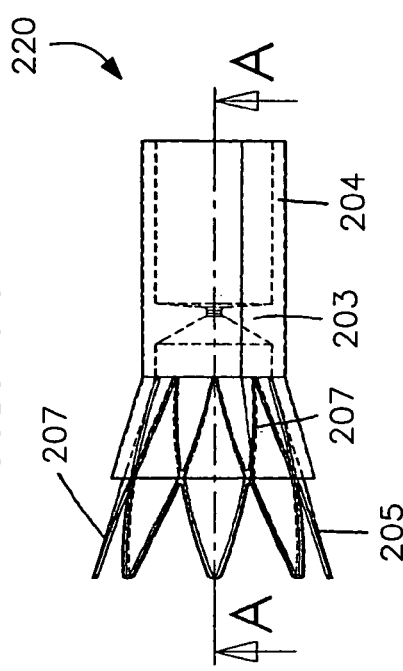
FIG. 76 is a side view of the device of FIG. 75.
Figure 77:
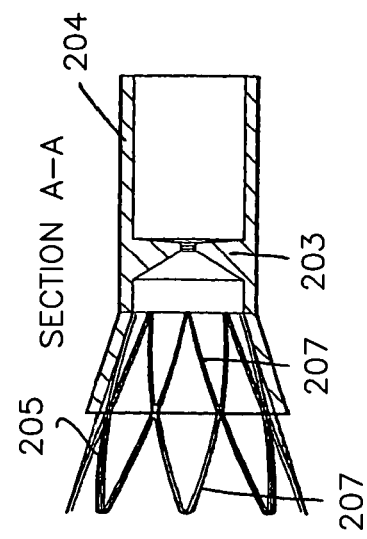
FIG. 77 is a view along line A-A in FIG. 76.
Figure 82:
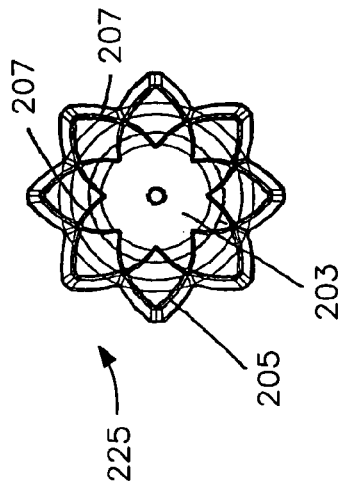
FIGS. 79 to 82 are views similar to FIGS. 75 to 78 of another medical treatment device according to the invention.
Figure 79:
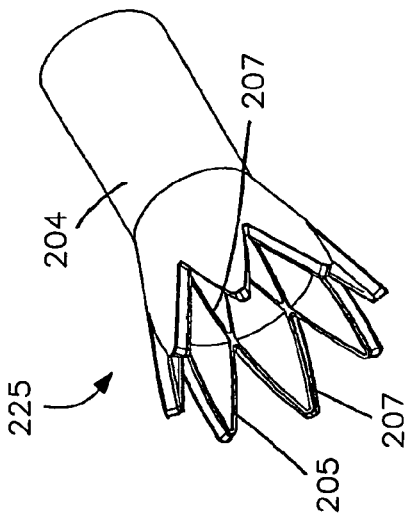
Figure 80:
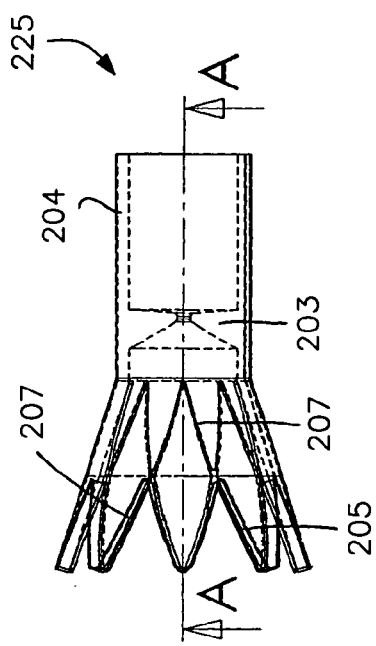
Figure 81:
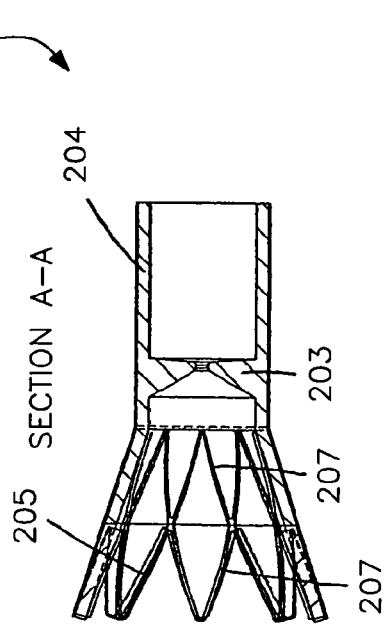
Figure 86:
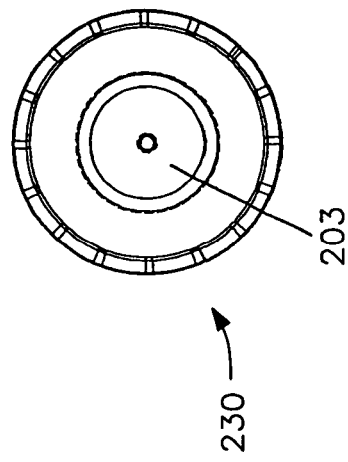
FIGS. 83 to 86 are views similar to FIGS. 75 to 78 of a further medical treatment device according to the invention.
Figure 83:
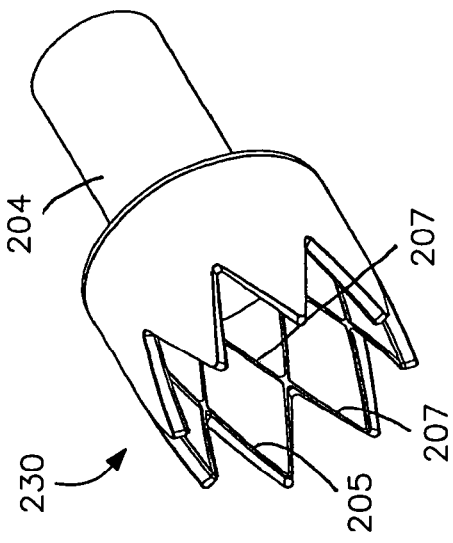
Figure 84:
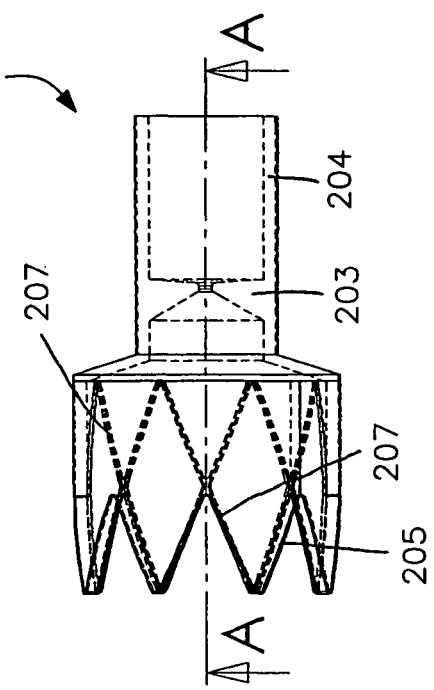
Figure 85:
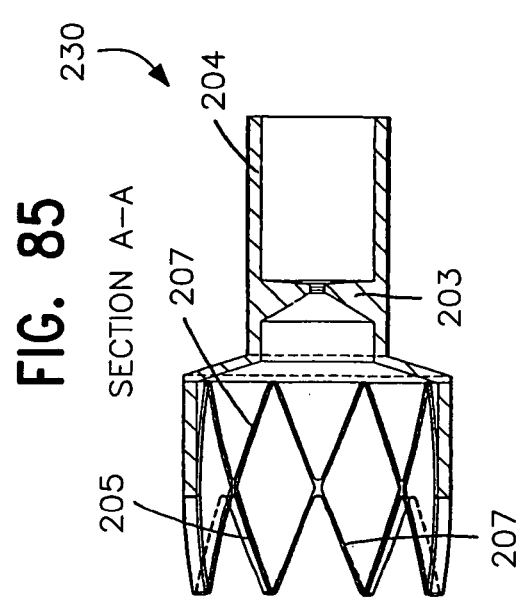
Figure 94:
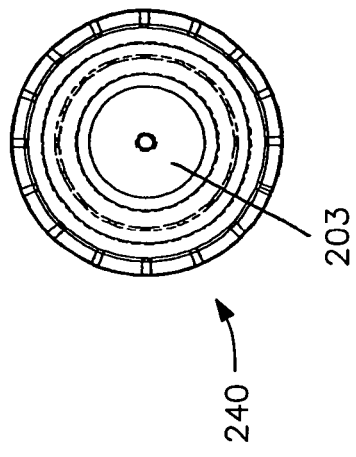
FIGS. 91 to 94 are views similar to FIGS. 75 to 78 of another medical treatment device according to the invention.
Figure 91:
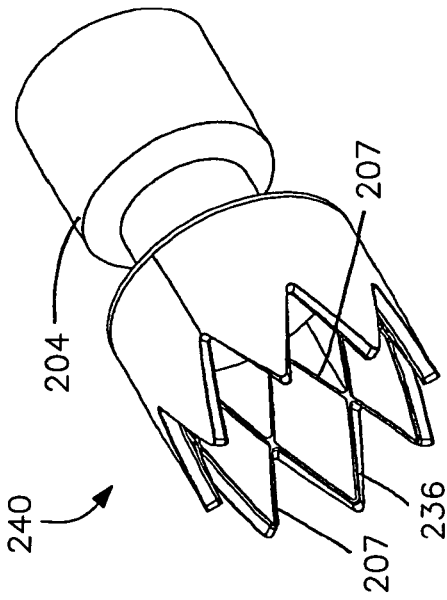
Figure 92:
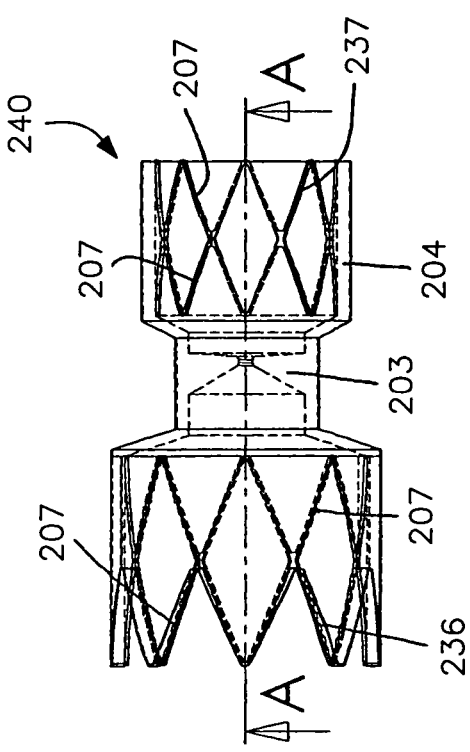
Figure 93:
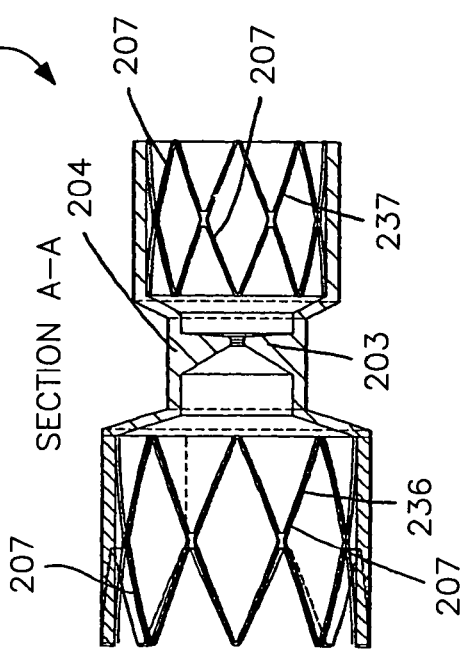
Figure 99:
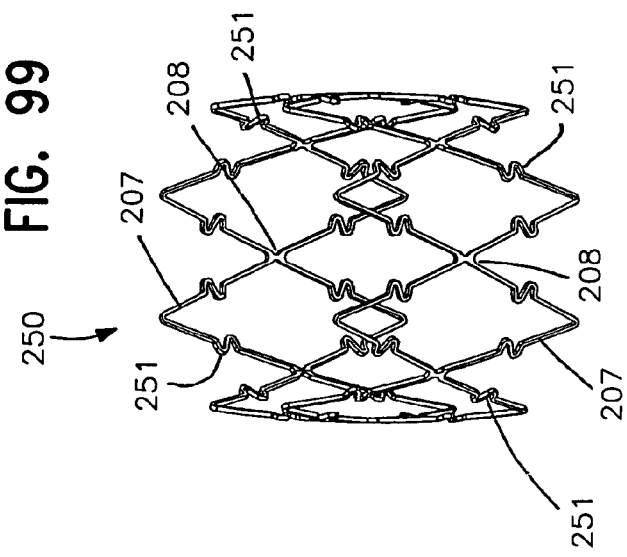
FIGS. 99 to 101 and 103 are views similar to FIGS. 27 to 30 of a support member of another medical treatment device according to the invention.

LES 300 open—anti-reflux barrier 203 stays compressed (FIG. 56).

LES 300 open for abnormally prolonged period of time—anti-reflux barrier 203 relaxes gradually so as to assume anti-reflux configuration (FIG. 57).

When the device 200 has been deployed in the oesophagus 202 and/or stomach 201, the therapeutic agent 209 may be delivered from the cell struts 210 in the lining member 204 to the inner surface of the oesophagus 202/stomach 201.

It will be appreciated that there are a variety of possible configurations for the valve member 203 and for the lining member 204. FIGS. 61 to 74 illustrate a variety of possible configurations for the valve member 203 and for the lining member 204.

FIGS. 61 to 74 illustrate a variety of different possible anti-reflux barrier geometrical designs. In FIG. 73 the distal side of the valve leaflet 206 is nicked. In FIG. 74 the valve member 203 is sliced.

In FIGS. 75 to 78 there is illustrated another medical treatment device 220 according to the invention, which is similar to the device 200 of FIGS. 26 to 60, and similar elements in FIGS. 75 to 78 are assigned the same reference numerals.

In this case the support member 205 extends proximally of the proximal end of the lining member 204.

FIGS. 79 to 82 illustrate a further medical treatment device 225 according to the invention, which is similar to the device 200 of FIGS. 26 to 60, and similar elements of FIGS. 79 to 82 are assigned the same reference numerals.

In this case the proximal region of the lining member 204 has a substantially zig-zag, wave pattern aligned with the proximal support element 207.

Referring to FIGS. 83 to 86 there is illustrated another medical treatment device 230 according to the invention, which is similar to the device 225 of FIGS. 79 to 82, and similar elements in FIGS. 83 to 86 are assigned the same reference numerals.

In this case the radial dimension of the support member 205 is substantially constant along the support member 205.

In FIGS. 87 to 90 there is illustrated another medical treatment device 235 according to the invention, which is similar to the device 230 of FIGS. 83 to 86, and similar elements in FIGS. 87 to 90 are assigned the same reference numerals.

In this case the device 235 comprises a proximal support member 236 and a distal support member 237. The two support members 236, 237 are substantially equal in size. The proximal support member 236 is located proximally of the valve member 203 and the distal support member 237 is located distally of the valve member 203.

FIGS. 91 to 94 illustrate a further medical treatment device 240 according to the invention, which is similar to the device 235 of FIGS. 87 to 90, and similar elements in FIGS. 91 to 94 are assigned the same reference numerals.

In this case the distal support member 237 is smaller in size than the proximal support member 236. In particular the radial dimension of the distal support member 237 is smaller than the radial dimension of the proximal support member 236.

Referring to FIGS. 95 to 98 there is illustrated another medical treatment device 245 according to the invention, which is similar to the device 200 of FIGS. 26 to 60, and similar elements in FIGS. 95 to 98 are assigned the same reference numerals.

In this case the support member 205 tapers distally radially outwardly. The support member 205 is arranged extending co-axially around the valve member 203.

FIGS. 75 to 98 illustrate a variety of different retention mechanism designs.

In FIGS. 99 to 103 there is illustrated a support member 250 of another medical treatment device according to the invention, which is similar to the device 200 of FIGS. 26 to 60, and similar elements in FIGS. 99 to 103 are assigned the same reference numerals.

In this case each support element 207 comprises two articulation regions 251 intermediate each coupling region 208 and the adjacent coupling region 208.

Figure 101:
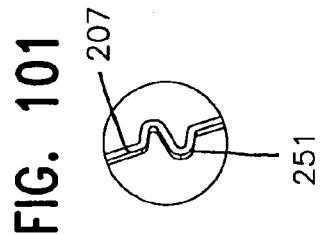
Figure 102:
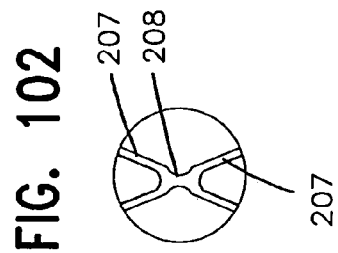
FIG. 102 is an enlarged, side view of a part of the support member of FIG. 100.
Figure 100:
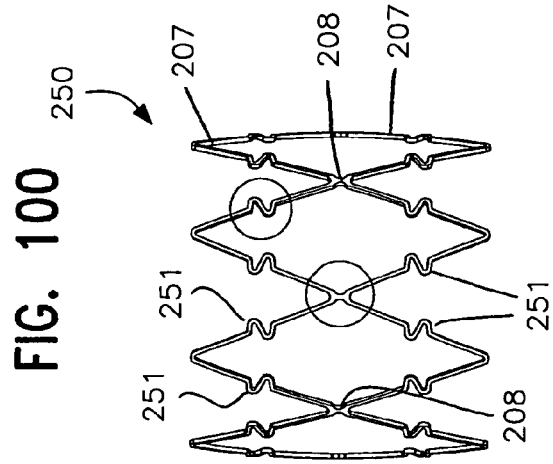
Figure 103:
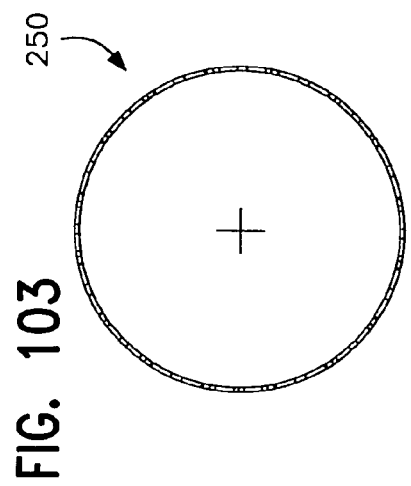

FIGS. 99 to 103 illustrate the retention mechanism with multiple articulation sites. FIG. 102 illustrates the first articulation site. FIG. 101 illustrates the second articulation site.

FIGS. 104 to 110 illustrate a support member 255 of a further medical treatment device according to the invention, which is similar to the device of FIGS. 99 to 103, and similar elements in FIGS. 104 to 110 are assigned the same reference numerals.

In this case each support element 207 comprises three articulation regions 256 intermediate each coupling region 208 and the adjacent coupling region 208.

FIGS. 104 to 110 illustrate the retention mechanism with multiple articulation sites. FIG. 106 illustrates the first articulation site. FIG. 107 illustrates the second articulation site. FIG. 109 illustrates the third articulation site.

FIGS. 27 to 30 and 99 to 110 illustrate features of the retention mechanism and desirable geometries.

Referring to FIGS. 1 to 25, there are illustrated various other medical devices according to the invention. In general the medical device may be a sleeve or prosthesis, as illustrated in one basic form in FIG. 6.

Figure 2:
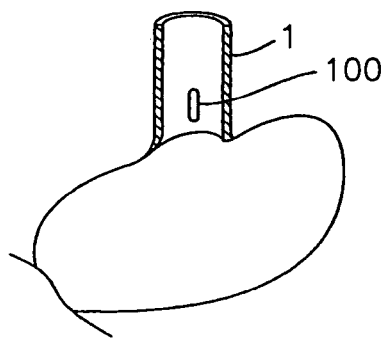
FIGS. 2 to 5 are partially cut-away, isometric views of the medical device and the delivery device of FIG. 1, in use.
Figure 3:
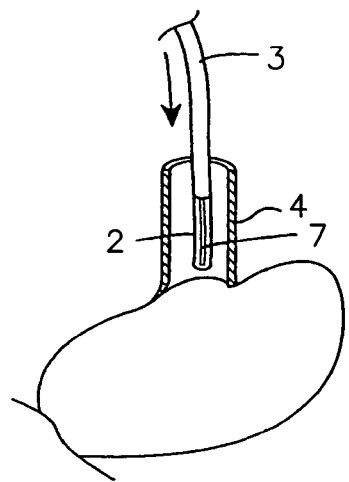
Figure 5:
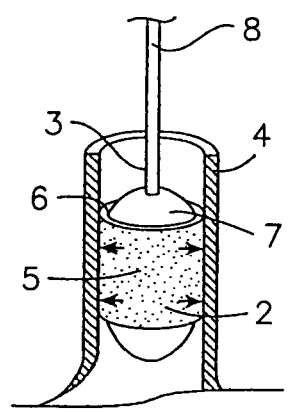
Figure 4:
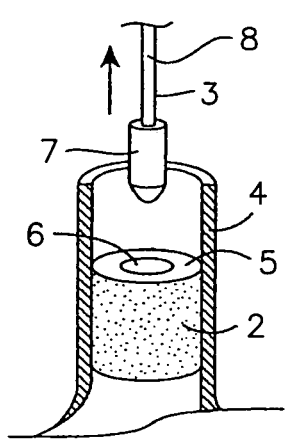
Figure 7:
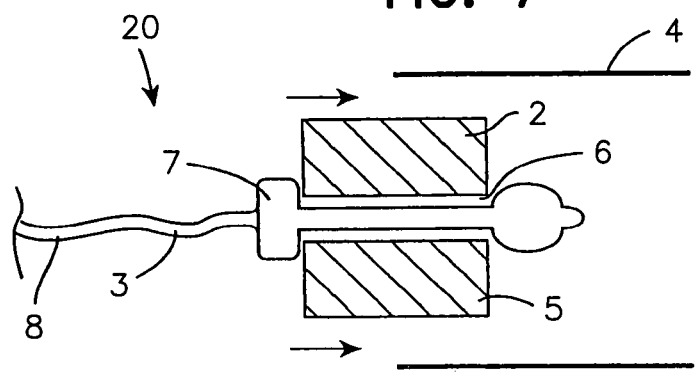
FIG. 7 is a cross-sectional, side view of another medical device according to the invention mounted to another delivery device according to the invention, in use.
Figure 8:
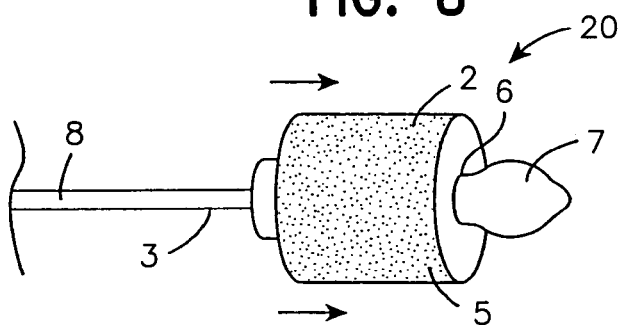
FIGS. 8 to 10 are isometric views of the medical device and the delivery device of FIG. 7, in use.
Figure 9:
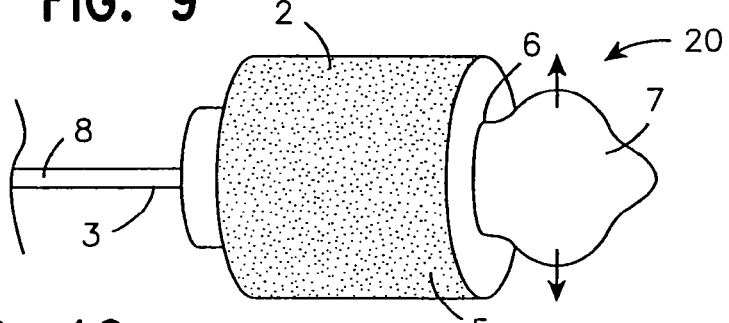

FIG. 1 is an illustration of a medical device loaded onto a delivery device. FIGS. 2 and 3 are cut away illustrations of the medical device at a deployment site. FIGS. 4 and 5 are close up illustrations of the medical device and deployment action.

The medical device of the invention may have various forms. Other than the form illustrated in FIG. 6, the medical device may take the form shown in FIGS. 18 to 25 for example, which is that of an elastic/visco elastic material twisted into form to provide a valving mechanism.

Figure 13:
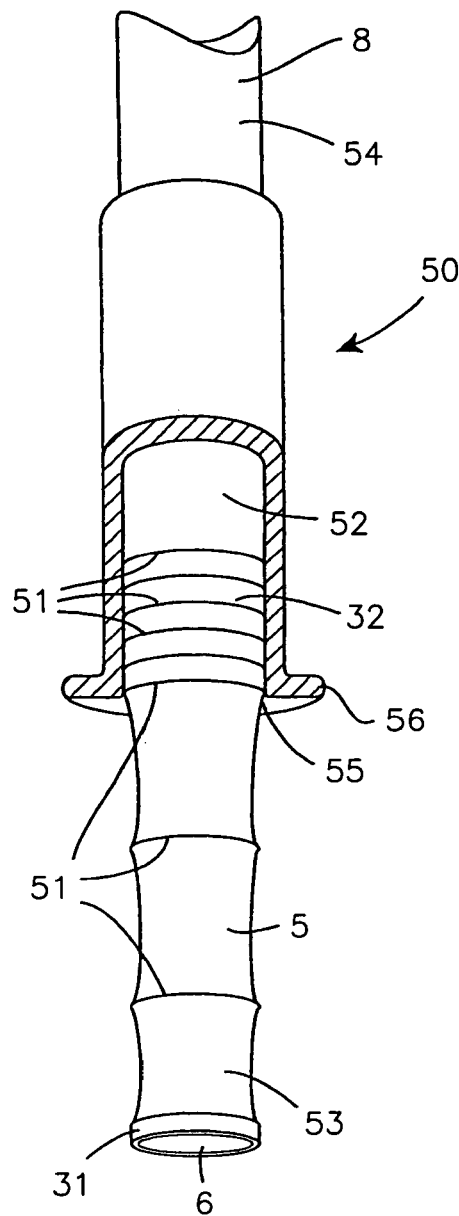
FIG. 13 is a partially cut-away, isometric view of another medical device according to the invention passing out of another delivery device according to the invention.
Figure 14:
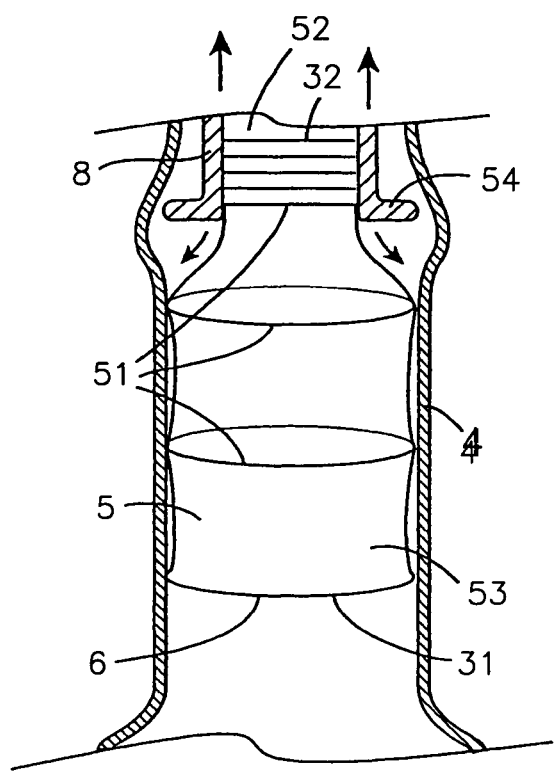
FIG. 14 is a partially cut-away, isometric view of the medical device and the delivery device of FIG. 13, in use.

The medical device of the invention may be deployed by means of a balloon catheter, as illustrated in FIGS. 7 to 10. The medical device may be deployed by means of a tube which may have shoulders to alleviate deployment, as FIGS. 13 and 14 illustrate.

Figure 16:
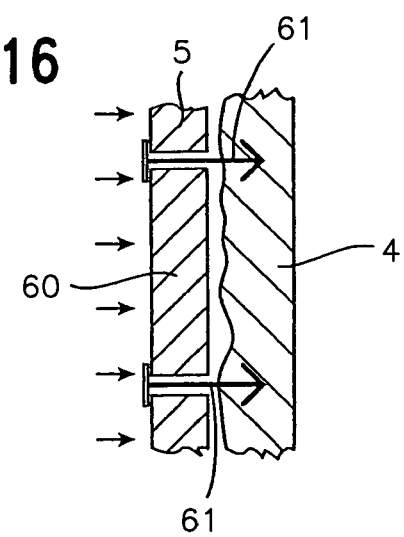
Figure 17:
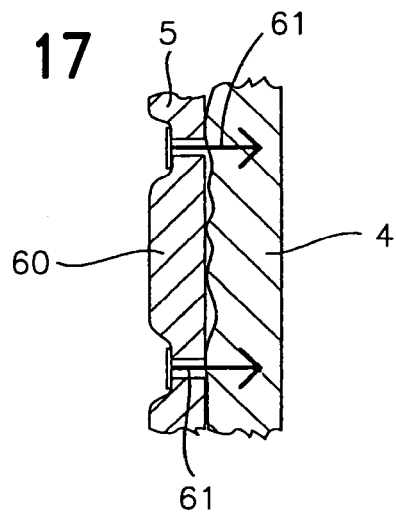
Figure 17A:
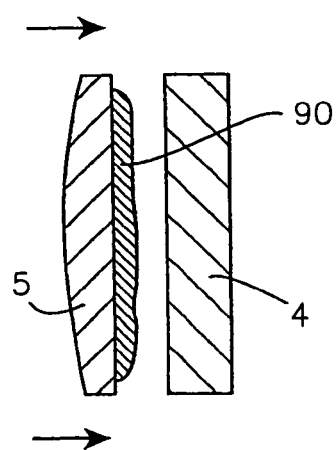
FIGS. 17(a) and 17(b) are cross-sectional, side views of another medical device according to the invention, in use.
Figure 17B:
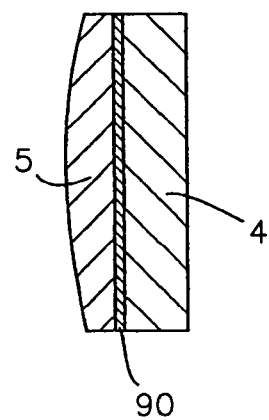
Figure 17D:
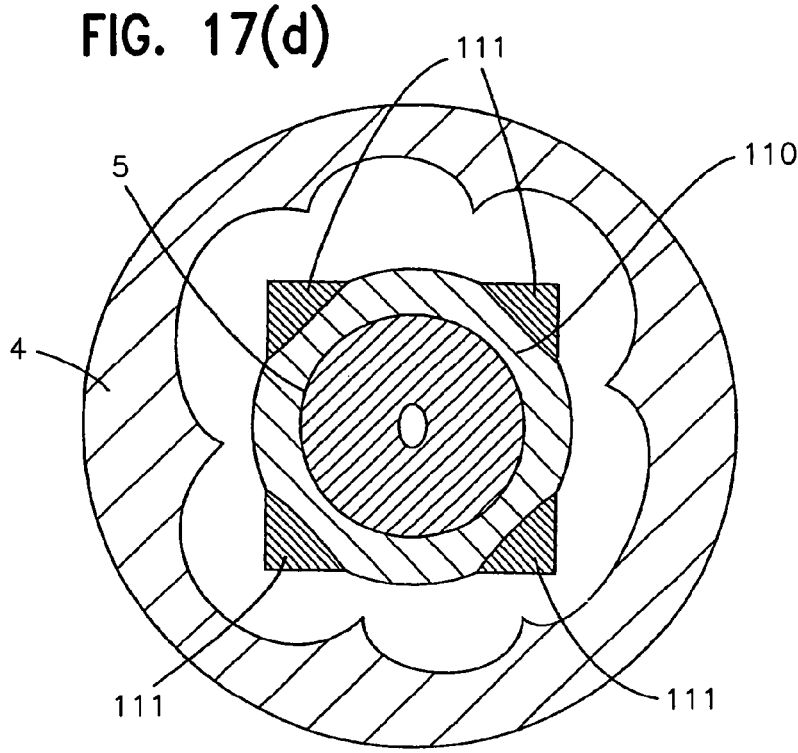
FIG. 17(d) is a cross-sectional, plan view of a further medical device according to the invention deployed in an alimentary canal.
Figure 17E:
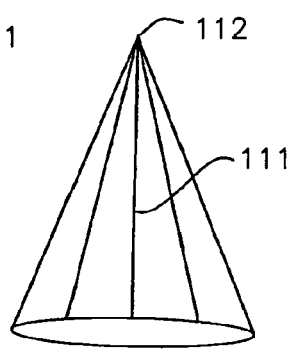
FIG. 17(e) is an isometric view of an anchor element of the medical device of FIG. 17(d)
Figure 17F:
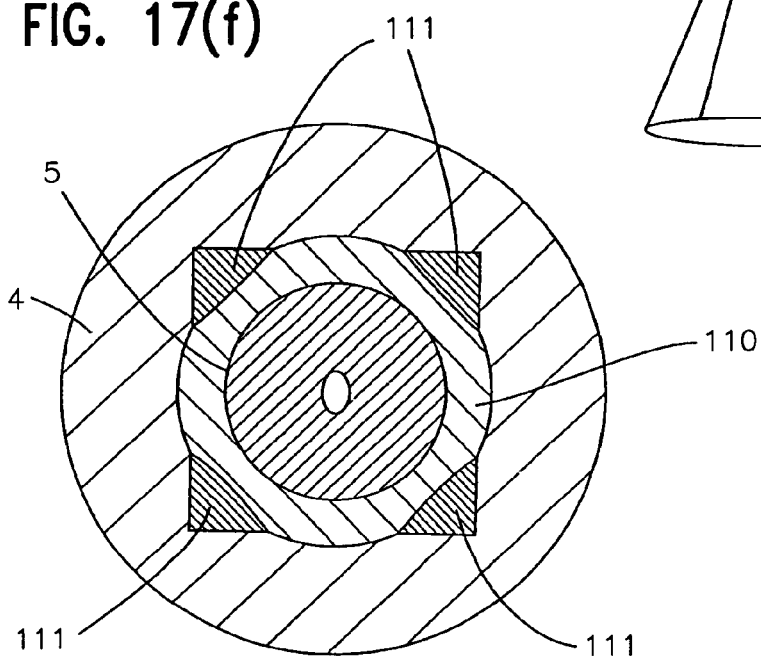
FIG. 17(f) is a cross-sectional, plan view of the medical device of FIG. 17(d) anchored to a wall of the alimentary canal.

The medical device may be retained in position by any of a number of possible mechanisms, such as adhesive (FIGS. 17(*a*) and 17(*b*)), rings (FIGS. 11 to 14), barbs (FIGS. 15 to 17), bullet form (FIGS. 17(*d*) to 17(*f*)).

Various embodiments of the medical device according to the invention are described in further detail as follows.

Referring to FIGS. 1 to 5 there is illustrated a medical kit 1 according to the invention comprising a medical device 2 and a delivery device 3. Together the medical device 2 and the delivery device 3 may be employed to treat a part of an inner surface of an alimentary canal, such as part of the inner surface of the oesophagus 4. The delivery device 3 is suitable for delivering the medical device 2 to a desired deployment location in the oesophagus 4.

The medical device 2 comprises a tubular sleeve 5 for lining part of the inner surface of the oesophagus 4. The sleeve 5 defines a lumen 6 through the sleeve 5. As illustrated in FIG. 5, the sleeve 5 may be employed to line around the entire circumference of part of the inner surface of the oesophagus 4.

The sleeve 5 has a contracted delivery configuration (FIG. 3) for delivery of the sleeve 5 through the oesophagus 4 to the desired deployment location, and an expanded deployment configuration (FIG. 4) for deployment at the desired deployment location in the oesophagus 4.

The sleeve 5 is of a polymeric material, in this case. The material of the sleeve 5 may be bioabsorbable and/or biodegradable.

The sleeve 5 may be loaded with a pharmaceutical agent to facilitate delivery of the pharmaceutical agent to the inner surface of the oesophagus 4.

The delivery device 3 comprises an expandable portion 7, in this case in the form of a balloon element, mounted to the distal end of an endoscope 8. The medical device 2 may be mounted over the balloon element 7. The balloon element 7 has a contracted delivery configuration (FIG. 3) for delivery of the medical device 2 through the oesophagus 4 to the desired deployment location in the oesophagus 4, and an expanded deployment configuration (FIG. 4) for deployment of the medical device 2 at the desired deployment location in the oesophagus 4.

In use, the sleeve 5 in the contracted delivery configuration is mounted around the balloon element 7 in the contracted delivery configuration. The delivery device 3 is then inserted through the patient's mouth and advanced through the oesophagus 4 until the sleeve 5 is located adjacent to the desired deployment location in the oesophagus 4 (FIG. 3).

The balloon element 7 is inflated to move the balloon element 7 from the contracted delivery configuration to the expanded deployment configuration, and thus move the sleeve 5 from the contracted delivery configuration to the expanded deployment configuration to deploy the sleeve 5 at the desired deployment location to line part of the inner surface of the oesophagus 4 (FIG. 4). In this manner, the oesophagus 4 may be treated. The balloon element 7 may then be deflated to move the balloon element 7 from the expanded deployment configuration to the contracted delivery configuration. During deflation, the sleeve 5 remains in the expanded deployment configuration, as illustrated in FIG. 5. The delivery device 3 with the balloon element 7 in the contracted delivery configuration is withdrawn from the oesophagus 4 (FIG. 5).

In this embodiment, the invention comprises:

1. The device 7, which connects to the end of the endoscope 8. The device 7 has an expandable component (delivery system), which, when expanded can apply a symmetrical radial pressure to the endothelium 4 of the gastric lumen within the gastrointestinal (GI) tract. Such a component could be an inflatable balloon or a mechanically expandable device, as shown in FIGS. 1 to 5.
2. The soft polymeric sleeve 5 (therapeutic component) that is loaded onto the outside of the expandable component 7. The soft polymeric sleeve 5 can be expandable and elastic, but may alternatively exhibit plastic deformation so that once expanded it retains its shape. The polymeric sleeve 5 may be inherently elastic but might be held in its expanded position by a plastically deformable support material. The polymeric sleeve 5 could additionally have a bio-adhesive outer surface.

The device comprising the delivery system 7 and the therapeutic component 5 can be attached to the end of the endoscope 8. A clinician can introduce the device into the gastric lumen and position it close to a wound or lesion 100. By expanding the delivery device 7, the therapeutic component 5 can be pressed against the gastric endothelium 4. The therapeutic component 5 can be retained at the site using either bio-adhesive or mechanical means or a combination of these.

FIG. 1 illustrates the endoscope 8 with the balloon 7. FIG. 2 illustrates the oesophageal lesion 100. FIG. 3 illustrates insertion of the polymeric sleeve 5 into the oesophageal lumen. FIG. 4 illustrates balloon inflation within the lumen. FIG. 5 illustrates sleeve adhesion.

In FIG. 6 there is illustrated another medical device 10 according to the invention, which is similar to the medical device 2 of FIGS. 1 to 5, and similar elements in FIG. 6 are assigned the same reference numerals.

The medical device 10 is suitable for being deployed in a curved or tortuous section 11 of the alimentary canal, as illustrated in FIG. 6, to line part of the inner surface of the alimentary canal.

FIG. 6 illustrates the tubular sleeve 5 conforming to a tortuous part of the gastrointestinal tract.

FIG. 6 illustrates the polymeric sleeve 5 implanted in a tortuous location.

Unlike a relatively rigid metal stent system, the polymeric sleeve 5 of the invention can conform to the tortuosity and irregularities of the GI tract, as illustrated in FIG. 6. This is important to optimise interfacial contact between the gastric endothelium 11 and the surface of the sleeve 5. Such a system can facilitate wound healing; wound protection and drug delivery profiles not achievable using alternative systems.

In addition polymeric sleeves can be designed to degrade over a pre-defined period of time, which is not possible with a metallic stent, which may have to be left in place.

Multiple polymeric sleeves can be loaded onto a single delivery device and can be overlapped in-situ without any of the problems associated with doing this using stents, such as reduction in endoluminal diameter, doubling of drug delivery dose at overlap points.

FIGS. 7 to 10 illustrate another medical kit 20 according to the invention, which is similar to the medical kit 1 of FIGS. 1 to 5, and similar elements in FIGS. 7 to 10 are assigned the same reference numerals.

The sleeve 5 may have a pre-defined elasticity and lumen size, as illustrated in FIGS. 7 to 10.

FIGS. 7 to 10 illustrates insertion of the device into the oesophagus 4 and inflation of the device followed by withdrawal of the balloon element 7.

In FIGS. 10(a) to 10(h) there is illustrated another medical device 80 according to the invention, which is similar to the medical device 2 of FIGS. 1 to 5, and similar elements in FIGS. 10(a) to 10(h) are assigned the same reference numerals.

In this case the sleeve 5 is of a viscoelastic foam, and is self expandable upon elapse of a predetermined period of time, for example 7 to 10 seconds, from a contracted deployment configuration (FIG. 10(e)) to an expanded deployment configuration (FIG. 10(g)) to seal the lumen 6 through the sleeve 5. The sleeve 5 is contractable from the expanded deployment configuration (FIG. 10(g)) to the contracted deployment configuration (FIG. 10(h)) by the compression force exerted by the walls of the oesophagus 4. The sleeve 5 is biased towards the expanded deployment configuration.

The medical device 80 is particularly suitable for use with an oesophagus experiencing transient lower oesophageal sphincter relaxation.

Erosion of an oesophagus by acid reflux may be mediated through a number of mechanisms. The relaxation of the lower oesophageal sphincter (LOS) is one cause of reflux. Relaxation of the LOS occurs normally during the swallowing process but may also occur transiently and randomly for no apparent reason, which is known as lower oesophageal relaxation (TLOSR). In some pathological conditions the LOS may be chronically relaxed. Hiatus hernia may result in incomplete LOS muscle contraction during which time reflux may be triggered by straining.

Upon swallowing, the walls of the oesophagus 4 expand to open the LOS 81 (FIG. 10(b)), to facilitate food or the like to pass through the LOS 81 into the stomach 82 (FIG. 10(c)). In the event where the LOS 81 closes normally, the sleeve 5 remains in the contracted deployment configuration throughout the swallowing process. As the sleeve 5 expands to the expanded deployment configuration only after elapse of 7 to 10 seconds, there is not sufficient time during the normal swallowing process for the sleeve 5 to expand. Upon closing of the LOS 81 the sleeve 5 in the contracted deployment configuration seals across the oesophagus 4 (FIG. 10(d)).

In the event of TLOSR, where the LOS 81 does not close normally after 7 to 10 seconds, the sleeve 5 expands to the expanded deployment configuration to seal across the oesophagus 4 to prevent acid reflux from the stomach 82 (FIG. 10(g)). Upon the eventual closure of the LOS 81, for example after elapse of 120 seconds, the sleeve 5 is compressed by the action of the walls of the oesophagus 4 to the contracted deployment configuration (FIG. 10(h)).

FIGS. 10(a) to 10(h) illustrates the sleeve shaped device 80 made from viscoelastic foam. The device 5, once secured, will expand to fill any opening in the LOS 81. In the event of closing of the LOS 81, the device 5 will compress significantly allowing the LOS 81 to function normally as illustrated by FIG. 10(d). The action of swallowing will open the LOS 81 and the lumen of the device 5 (FIGS. 10(b) and 10(c)) but the device 5 will not expand unless the LOS 81 is open for a prolonged period of time. If the LOS 81 opens transiently (TLOSR) for longer than 10 seconds (FIG. 10(e)), the device 5 will expand thus closing the open oesophageal lumen (FIG. 10(g)).

The medical device 80 addresses the problem of TLOSRs specifically and does not result in impaired normal swallowing. The expansion functions only during TLOSRs but remains inactive during normal swallowing induced muscle relaxation. Considering that normal swallowing causes a 4 to 7 second relaxation of the LOS 81, whereas TLOSR causes a relaxation of up to 120 seconds, the medical device 80 has a time-dependant mode of action.

Figure 10:
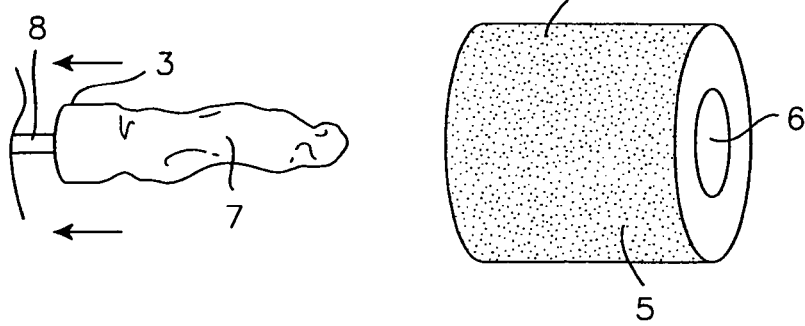
Figure 10I:
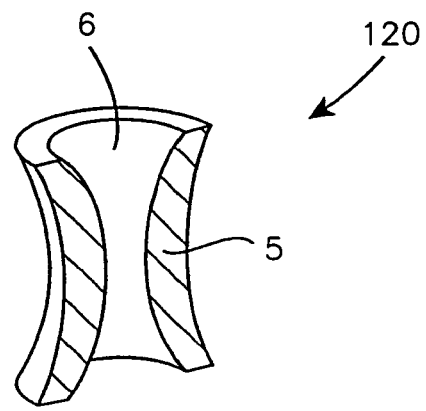
FIG. 10(i) is a cut-away, isometric view of another medical device according to the invention.

FIG. 10(i) illustrates another medical device 120 according to the invention, which is similar to the medical device 2 of FIGS. 1 to 5, and similar elements in FIG. 10(i) are assigned the same reference numerals.

In this case the radial dimension of the outer surface of the sleeve 5 varies along the sleeve 5 and the radial dimension of the inner surface of the sleeve 5 varies along the sleeve 5. In particular the outer surface of the sleeve 5 tapers inwardly from each end towards the centre of the sleeve 5, and the inner surface of the sleeve 5 tapers inwardly from each end towards the centre of the sleeve 5.

The device 120 may take the form of the elastic material as shown in FIG. 10(i). The elastic material by its nature creates a valve by closing in the centre thus pulling the tissue, that the sleeve 5 is lining, inwardly.

Figure 10J:
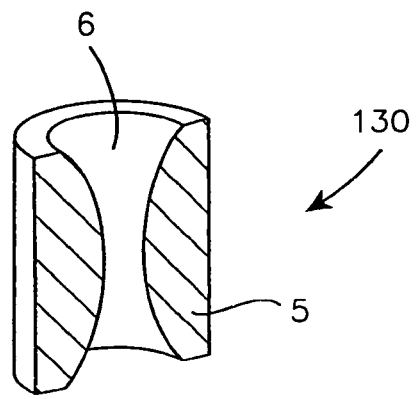
FIG. 10(j) is a cut-away, isometric view of a further medical device according to the invention.

Referring to FIG. 10(j) there is illustrated another medical device 130 according to the invention, which is similar to the medical device 120 of FIG. 10(i), and similar elements in FIG. 10(j) are assigned the same reference numerals.

In this case the radial dimension of the outer surface of the sleeve 5 is substantially constant along the sleeve 5.

The device 130 may be of a foam so that it forms a valve in the gastrointestinal tract. The foam may be designed to allow materials to pass into the stomach by means of peristaltic action.

Figure 11:
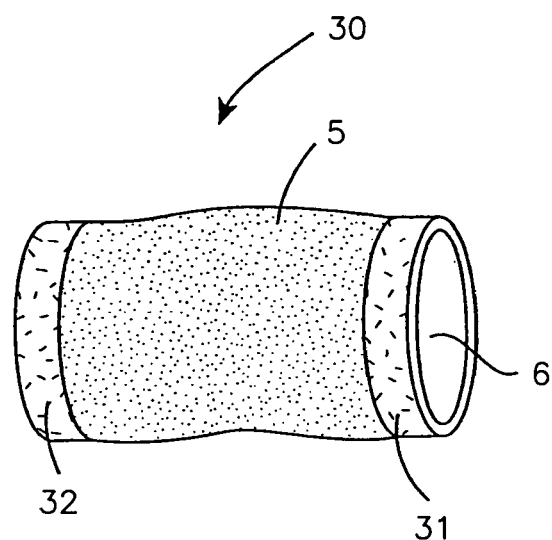
FIG. 11 is an isometric view of another medical device according to the invention.

Referring to FIG. 11 there is illustrated another medical device 30 according to the invention, which is similar to the medical device 2 of FIGS. 1 to 5, and similar elements in FIG. 11 are assigned the same reference numerals.

In this case the medical device 30 comprises a first support ring 31 at a first end of the sleeve 5 and a second support ring 32 at a second end of the sleeve 5 spaced-apart from the first support ring 31. Together the support rings 31, 32 acts as support elements to support the sleeve 5 in the expanded deployment configuration lining part of the inner surface of the oesophagus 4.

The support rings 31, 32 may be coupled to the sleeve 5 in any suitable manner. For example the support rings 31, 32 may be embedded within the sleeve 5. Alternatively the support rings 31, 32 may be provided externally of the sleeve 5, and the support rings 31, 32 may be configured to engage the inner surface of the sleeve 5.

The polymeric sleeve 5 may have one or more supporting rings 31, 32 to ensure a tight fit to the lumen of the GI tract, as shown in FIG. 11. The rings 31, 32 may be expandable or rigid and may be attached to the sleeve 5 or may be positioned separately. The expandable rings 31, 32 may be made from elastically or plastically deformable material.

The sleeve 5 may have rings with different sizes to enable fitting to irregularly shaped spaces.

Alternatively small elastic rings may be placed in the centre of the sleeve 5 to form a "sphincter" like structure.

FIG. 11 illustrates the elastomeric/hydrogel material 5 and the supporting rings 31, 32 of varying width.

FIG. 11 illustrates the polymeric sleeve 5 with the supporting rings 31, 32 of similar size.

Figure 12:
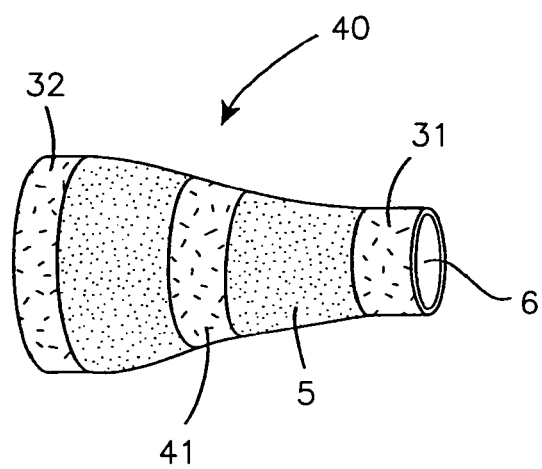
FIG. 12 is an isometric view of a further medical device according to the invention.

In FIG. 12 there is illustrated a further medical device 40 according to the invention, which is similar to the medical device 30 of FIG. 11, and similar elements in FIG. 12 are assigned the same reference numerals.

In this case the medical device 40 comprises a third support ring 41 intermediate the first support ring 31 and the second support ring 32.

The sleeve 5 is substantially frusto-conically shaped, having a smaller diameter adjacent to the first support ring 31 than adjacent to the second support ring 32.

FIG. 12 illustrates the numerous supporting rings 31, 32, 41 and the soft conforming elastomeric/hydrogel 5.

FIG. 12 illustrates the polymeric sleeve 5 with the supporting rings 31, 32, 41 of varying size.

FIGS. 13 and 14 illustrate another medical kit 50 according to the invention, in which the medical device is similar to the medical device 30 of FIG. 11 and the delivery device is similar to the delivery device 3 of FIGS. 1 to 5, and similar elements in FIGS. 13 and 14 are assigned the same reference numerals.

In this case the medical device 53 comprises a plurality of support rings 51 between the first support ring 31 and the second support ring 32. The support rings 51 are spaced-apart along the sleeve 5.

The medical device 53 has a shortened delivery configuration in which the support rings 31, 32, 51 are closely adjacent one another, and an elongated deployment configuration in which the support rings 31, 32, 51 are spaced-apart from one another.

The delivery device 54 comprises the endoscope 8 and an ejector housed within the endoscope 8. In the delivery configuration the ejector is spaced proximally of a distal end of the endoscope 8 to create a reception space 52 at the distal end of the endoscope 8 for receiving the medical device 53 for delivery of the medical device 53 through the oesophagus 4 to the desired deployment location.

The endoscope 8 has an outlet 55 at the distal end of the reception space 52. A radially outwardly protruding shoulder 56 is provided extending around the circumference of the outlet 55.

The ejector is movable distally relative to the endoscope 8 from the delivery configuration to the deployment configuration to pass the medical device 53 out of the reception space 52 through the outlet 55 to deploy the medical device 53 at the desired deployment location in the oesophagus 4.

In use, the medical device 53 is arranged in the shortened delivery configuration with the support rings 31, 32, 51 closely adjacent one another and loaded into the reception space 52 of the endoscope 8. The delivery device 54 is then inserted through the patient's mouth and advanced through the oesophagus 4 until the outlet 55 is adjacent to the desired deployment location in the oesophagus 4.

To deploy the medical device 53 out of the reception space 52, the ejector is maintained in a fixed position and the endoscope 8 is withdrawn proximally, thus causing the medical device 53 to pass out of the reception space 52 through the outlet 55 (FIG. 14). As the medical device 53 is deployed the support rings 31, 32, 51 move apart from one another and thus the medical device 53 is deployed in the oesophagus 4 in the elongated deployment configuration to line the inner surface of the oesophagus 4. In this manner the oesophagus 4 may be treated. When the medical device 53 has been fully deployed, the delivery device 54 is withdrawn from the oesophagus 4.

The polymeric sleeve 5 is loaded into a dispensing tube that fits onto the end of the endoscope 8. Contained within the dispensing tube is the expandable polymeric sleeve 5 that may be ribbed or segmented, and the required length can be dispensed and detached from the dispenser 52, as shown in FIG. 13. The dispenser has a raised edge 56 that allows the oesophageal tissue 4 to be lifted out of the way during use, as shown in FIG. 14.

FIG. 13 illustrates the segment detachment point 55.

FIG. 13 illustrates the device for dispensing segmented polymeric sleeves 5 from the end of the endoscope 8.

Figure 15:
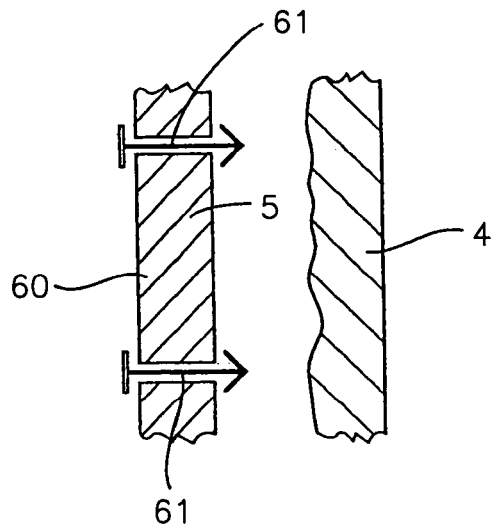
FIGS. 15 to 17 are cross-sectional, side views of another medical device according to the invention, in use.

FIG. 14 illustrates the device dispensing a segmented polymeric sleeve 5 into the gastric lumen Referring to FIGS. 15 to 17 there is illustrated another medical device 60 according to the invention, which is similar to the medical device 2 of FIGS. 1 to 5, and similar elements in FIGS. 15 to 17 are assigned the same reference numerals.

In this case the medical device 2 comprises a plurality of anchor elements 61 extending through the sleeve 5. Upon inflation of the balloon element 7, the anchor elements 61 are extendable into the wall of the oesophagus 4 to engage the oesophagus wall, and thereby anchor the sleeve 5 to the oesophagus wall. In this manner the sleeve 5 is supported in the expanded deployment configuration lining part of the inner surface of the oesophagus 4.

The exterior of the sleeve 5 could have an adhesive layer or securing mechanism (FIGS. 15 to 17), which, when expanded using the balloon 7 in the oesophagus 4 adheres to the oesophageal endothelium. Upon relaxation, the sleeve 5 will pull the sphincter closed.

This device could be used to improve the effectiveness of the oesophageal sphincter and could be adjusted on demand by the surgeon.

FIGS. 15 to 17 illustrates a securement mechanism in use, where clips 61 are pushed through the wall of the oesophagus 4 by device expansion, such as balloon inflation.

It will be appreciated that a range of means may be employed to support the sleeve 5 lining part of the inner surface of the oesophagus 4. For example, the sleeve 5 may be attached to the inner surface of the oesophagus 4, such as by means of an adhesive 90, as illustrated in FIGS. 17(*a*) and 17(*b*).

Referring to FIGS. 17(*d*) to 17(*f*) there is illustrated another medical device 110 according to the invention, which is similar to the medical device 60 of FIGS. 15 to 17, and similar elements in FIGS. 17(*d*) to 17(*f*) are assigned the same reference numerals.

In this case the medical device 110 comprises four anchor elements 111 mounted to the exterior surface of the sleeve 5. Each anchor element 111 is conically shaped with a pointed tip 112 to form a substantially bullet shaped retainer element. The anchor elements 111 are extendable into the wall of the oesophagus 4 to engage the oesophagus wall, and thereby anchor the sleeve 5 to the oesophagus wall. In this manner the sleeve 5 is supported in the expanded deployment configuration lining part of the inner surface of the oesophagus 4 (FIG. 17(*f*)).

In FIGS. 18 to 25 there is illustrated a further medical device 70 according to the invention, which is similar to the medical device 2 of FIGS. 1 to 5, and similar elements in FIGS. 18 to 25 are assigned the same reference numerals.

In this case the sleeve 5 is twistable to move the sleeve 5 between an open configuration (FIGS. 18 and 22) in which the lumen 6 is open, and a sealed configuration (FIGS. 21 and 25) in which the lumen 6 is closed.

The implantable sleeve 5 described above could have an "hourglass" shape, as illustrated in FIGS. 18 to 21. This shape would enable the device to be located and secured at the oesophageal sphincter. In addition the device can be twisted in-situ by the clinician to tailor the elasticity of the orifice created. The sleeve 5 could be held in place either by sutures or by an adhesive.

FIGS. 18 to 21 illustrate the sleeve 5 designed as a sphincter implant with adjustable opening tightness.

In another embodiment of the invention, the delivery device comprises a cover element slidably mounted to the endoscope 8. The cover element is movable relative to the endoscope 8 between a delivery configuration in which the medical device is restrained beneath the cover element, and a deployment configuration in which the cover element is retracted to uncover the medical device and thus facilitate deployment of the medical device.

The invention has been described above with reference to FIGS. 1 to 25 in relation to treatment of the inner surface of an oesophagus. However it will be appreciated that the invention may be employed to treat the inner surface of other parts of the alimentary canal, such as the inner surface of the stomach or the inner surface of the colon. In such cases the medical device may be configured to line part of the inner surface of the stomach or part of the inner surface of the colon, and the delivery device may be configured to deliver the medical device to a deployment location in a stomach or in a colon.

It will be appreciated that the medical device may be configured to line around only part of the circumference of part of the inner surface of the alimentary canal. In this case the medical device may be provided in the form of a patch or a prosthesis.

ALTERNATIVE APPLICATIONS

An application other than erosive gastric disease that would benefit from the invention is gastric cancer. Current treatment involves saturating the gastric tissue with highly toxic chemotherapeutic agents, which give rise to unpleasant side effects. Facilitating the localisation or targeting of such drugs to a specific site will significantly reduce the dosage required and improve the therapeutic efficacy. Specifically, cancers of the oesophagus, colon and biliary tree could be treated using this approach.

Other indications that could be targeted with this therapeutic approach are wound healing of caustic burns, radiotherapy induced lesions or post-surgical trauma. The invention may be useful in the prevention of stricture and anastamotic leakage.

The invention may be employed for localised and prolonged treatment of ulcerative colitis, eosinophilic colitis and inflammatory bowel disease.

The invention is not limited to the embodiments hereinbefore described, with reference to the accompanying drawings, which may be varied in construction and detail.

The invention claimed is:

1. A medical device for placement in a sphincter muscle in a gastrointestinal tract, the device comprising:
   a valve member comprising valve portions, the valve member and valve portions comprising a hydrolytically and oxidatively stable biomimetic cellular viscoelastic foam to modify the functioning of the sphincter muscle, the foam being configured to viscoelastically compress and distend in a manner that mechanically augments the action of the sphincter muscle;
   a support member which is engagable with a wall of the gastrointestinal tract to support the valve member in the sphincter muscle;
   wherein the valve portions extend substantially radially inwardly of the support member, the valve portions having an open configuration to facilitate passage of material through the valve member, and a restriction configuration to obstruct flow through the valve member, the valve portions being configured to move between the restriction configuration and the open configuration in response to peristalsis within the gastrointestinal tract, and the valve members being configured to move gradually over a period of at least one second between the open configuration and the restriction configuration due to the viscoelasticity of the foam.

2. A device as claimed in claim 1 wherein the valve member comprises a polyurethane material.

3. A device as claimed in claim 1 wherein the support member is substantially tubular.

4. A device as claimed in claim 1 wherein the support member extends distally of the valve member.

5. A device as claimed in claim 1 wherein the support member extends proximally of the valve member.

6. A device as claimed in claim 1 wherein the support member is tapered.

7. A device as claimed in claim 6 wherein the support member tapers proximally radially inwardly.

8. A device as claimed in claim 1 wherein the support member comprises a shape memory material.

9. A device as claimed in claim 8 wherein the support member comprises Nitinol.

10. A device as claimed in claim 1 wherein the support member comprises a stent.

11. A device as claimed in claim 1 wherein the support member is extendable into a wall of a gastrointestinal tract.

12. A device as claimed in claim 1 wherein the device comprises a lining member for lining a part of the gastrointestinal tract.

13. A device as claimed in claim 12 wherein the lining member is located radially outwardly of the valve member.

14. A device as claimed in claim 12 wherein the lining member is located radially inwardly of the support member.

15. A device as claimed in claim 12 wherein the support member is provided external of the lining member.

16. A device as claimed in claim 12 wherein the support member is engagable against an inner surface of the lining member.

17. A device as claimed in claim 12 wherein the support member is at least partially embedded within the lining member.

18. A device as claimed in claim 12 wherein the support member extends through the lining member.

19. A device as claimed in claim 1 wherein the support member is a distal support member, the device further comprising a proximal support member.

20. A device as claimed in claim 19 wherein the proximal support member is larger than the distal support member.

21. A device as claimed in claim 20 wherein the radial dimension of the proximal support member is larger than the radial dimension of the distal support member.

22. A device as claimed in claim 20 wherein the proximal support member is of equal size to the distal support member.

23. A device as claimed in claim 12 wherein the lining member is of a polymeric material.

24. A device as claimed in claim 1 wherein the valve member has a connecting portion for mounting to the support member.

25. A device as claimed in claim 1 wherein the support member comprises a proximal flare.

* * * * *